(12) United States Patent
Hee-Hanson et al.

(10) Patent No.: US 12,274,875 B1
(45) Date of Patent: Apr. 15, 2025

(54) NEEDLE SHROUD LATCH FOR INJECTION DEVICES

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/620,586

(22) Filed: Mar. 28, 2024

(51) Int. Cl.
| | |
|---|---|
| *A61M 5/32* | (2006.01) |
| *A61M 5/20* | (2006.01) |
| *A61M 5/315* | (2006.01) |
| *A61M 5/50* | (2006.01) |

(52) U.S. Cl.
CPC ........ *A61M 5/3257* (2013.01); *A61M 5/2033* (2013.01); *A61M 5/31505* (2013.01); *A61M 5/31571* (2013.01); *A61M 5/50* (2013.01); *A61M 2005/2013* (2013.01); *A61M 2005/206* (2013.01); *A61M 2005/208* (2013.01); *A61M 2005/3247* (2013.01)

(58) Field of Classification Search
CPC ........ A61M 5/3257; A61M 2005/3247; A61M 2005/3243
See application file for complete search history.

(56) References Cited

U.S. PATENT DOCUMENTS

| | | | | |
|---|---|---|---|---|
| 4,900,311 | A | * | 2/1990 | Stern ................... A61M 5/3271 604/263 |
| 5,088,986 | A | * | 2/1992 | Nusbaum ............ A61M 5/3271 604/198 |
| 5,290,256 | A | * | 3/1994 | Weatherford ....... A61M 5/3271 604/263 |
| 5,688,241 | A | | 11/1997 | Asbaghi |
| 7,597,685 | B2 | | 10/2009 | Olson |
| 8,016,797 | B2 | | 9/2011 | Gratwohl et al. |
| 8,821,451 | B2 | | 9/2014 | Daniel |
| 9,199,038 | B2 | | 12/2015 | Daniel |

(Continued)

FOREIGN PATENT DOCUMENTS

| | | |
|---|---|---|
| WO | WO 2011/123024 A1 | 10/2011 |
| WO | WO 2014/115241 A1 | 7/2014 |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Jenna Zhang
(74) *Attorney, Agent, or Firm* — Fish & Richardson P.C.

(57) ABSTRACT

An injection device includes a housing, a needle shroud movable within the housing between an extended position and a retracted position, and a needle shroud latch configured to hold the needle shroud in its retracted position. The needle shroud latch includes a button arranged at the housing such that a user can actuate the button by applying an actuation force to the button to hold the needle shroud in its retracted position.

26 Claims, 11 Drawing Sheets

(56) References Cited

U.S. PATENT DOCUMENTS

| | | | |
|---|---|---|---|
| 9,408,976 B2 | 8/2016 | Olson et al. | |
| 9,498,579 B2 | 11/2016 | Ruan | |
| 9,662,452 B2 | 5/2017 | Daniel | |
| 9,867,940 B2 | 1/2018 | Holmqvist et al. | |
| 9,919,107 B2 | 3/2018 | Imai et al. | |
| 10,420,898 B2 | 9/2019 | Daniel | |
| 11,369,751 B2 | 6/2022 | Ruan et al. | |
| 11,944,787 B2 | 4/2024 | Franke | |
| 2006/0276756 A1* | 12/2006 | Francavilla | A61M 5/3257 604/197 |
| 2010/0268170 A1* | 10/2010 | Carrel | A61M 5/2033 604/198 |
| 2012/0203186 A1 | 8/2012 | Vogt et al. | |
| 2013/0041328 A1 | 2/2013 | Daniel | |
| 2013/0096512 A1* | 4/2013 | Ekman | A61M 5/3257 604/197 |
| 2013/0123710 A1* | 5/2013 | Ekman | A61M 5/3257 604/198 |
| 2013/0261559 A1* | 10/2013 | Werbickas | A61M 5/3257 604/198 |
| 2014/0025013 A1 | 1/2014 | Dowds et al. | |
| 2015/0190580 A1 | 7/2015 | Imai et al. | |
| 2015/0258283 A1 | 9/2015 | Imai et al. | |
| 2016/0089498 A1 | 3/2016 | Daniel | |
| 2018/0064875 A1 | 3/2018 | Holmqvist | |
| 2018/0361082 A1 | 12/2018 | Sall et al. | |
| 2020/0289755 A1 | 9/2020 | Franke | |
| 2021/0236732 A1 | 8/2021 | Chu et al. | |
| 2021/0244887 A1* | 8/2021 | Halseth | A61M 5/3159 |
| 2021/0393886 A1* | 12/2021 | Nicolas | A61M 5/24 |
| 2022/0387719 A1 | 12/2022 | Wang et al. | |
| 2022/0395642 A1 | 12/2022 | Karlsson | |
| 2024/0139430 A1 | 5/2024 | Chansavang et al. | |
| 2024/0165346 A1* | 5/2024 | Chansavang | A61M 5/3257 |

FOREIGN PATENT DOCUMENTS

| | | |
|---|---|---|
| WO | WO 2021/008839 A1 | 1/2021 |
| WO | WO 2023/104512 A1 | 6/2023 |

OTHER PUBLICATIONS

U.S. Appl. No. 18/619,754, filed Mar. 28, 2024, Alexander Hee-Hanson.

U.S. Appl. No. 18/619,991, filed Mar. 28, 2024, Alexander Hee-Hanson.

U.S. Appl. No. 18/620,210, filed Mar. 28, 2024, Alexander Hee-Hanson.

U.S. Appl. No. 18/619,996, filed Mar. 28, 2024, Alexander Hee-Hanson.

U.S. Appl. No. 18/620,097, filed Mar. 28, 2024, Alexander Hee-Hanson.

* cited by examiner

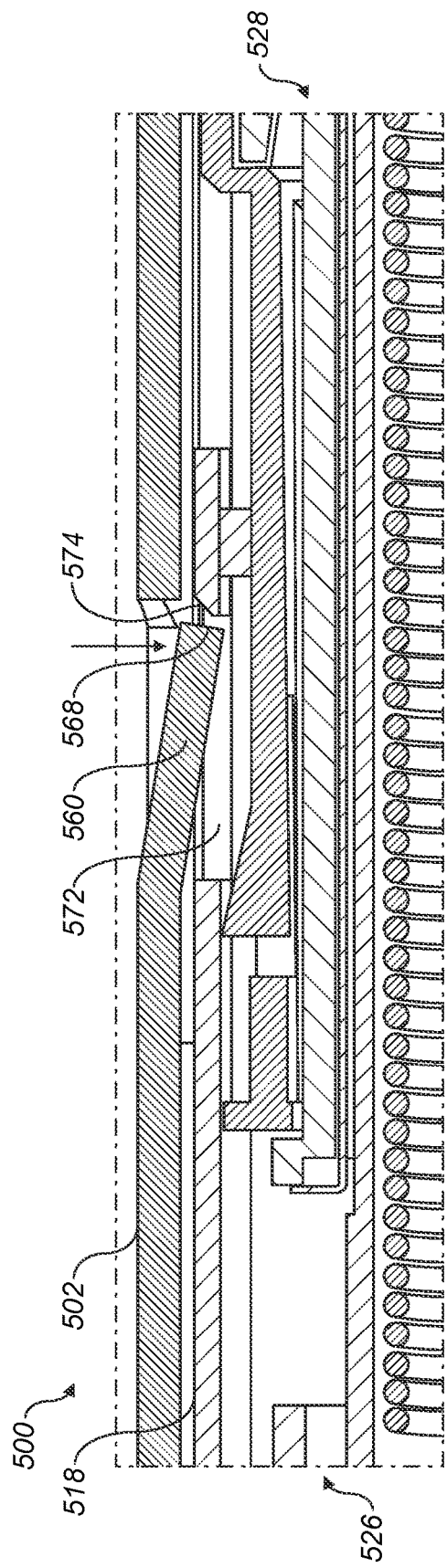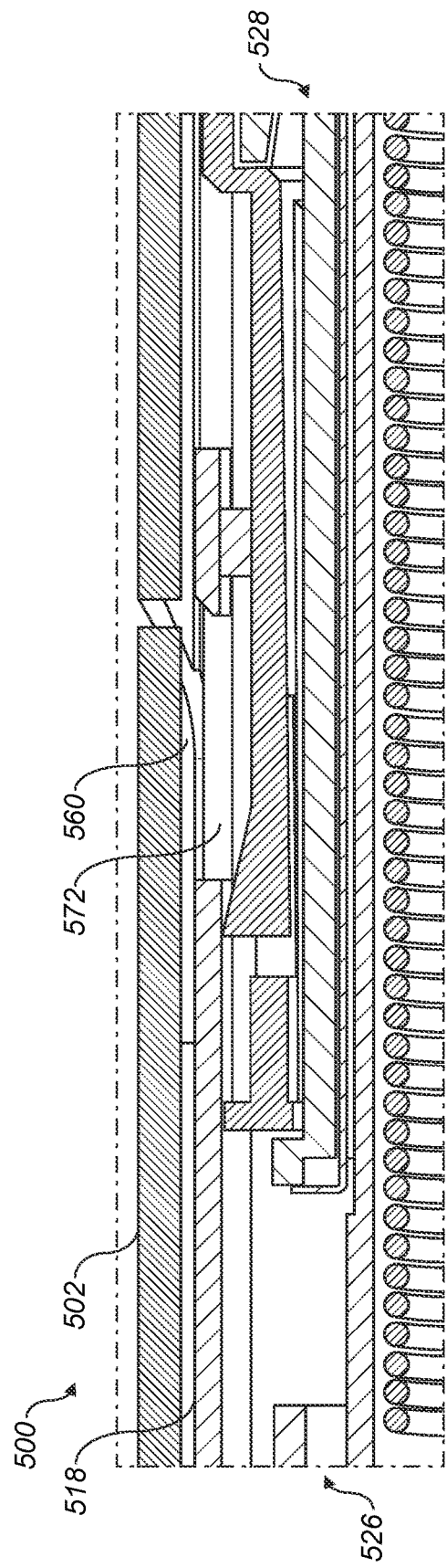

NEEDLE SHROUD LATCH FOR INJECTION DEVICES

TECHNICAL FIELD

This application relates to an injection device for delivery of a medicament, particularly to an auto-injector device.

BACKGROUND

An auto-injector may be described as a device which completely or partially replaces the activities involved in drug delivery from a standard syringe. Typically, these include removal of the protective syringe cap, insertion of the needle, injection of drug and possibly removal and shielding of the used needle. Administering an injection is a process which presents several risks and challenges, both mental and physical. The use of an auto-injector can bring many benefits for the user and healthcare professional.

Many auto-injectors have a needle cover which is biased by a spring (the needle cover spring) to extend out of the device. On removal of the device from the injection site, this spring automatically extends the needle cover past the needle to provide needle shielding. On activation of the device, the needle cover is pushed into the device. A user has to provide the force to actuate the needle cover, overcome the activation mechanism forces and compress the needle cover spring (activation force). During drug delivery the user holds the device at the injection site and applies a force (hold force) parallel to the needle cover direction of extension to react the needle cover biasing member.

If the activation or hold force is too high or has a certain profile, it can lead to use issues such as incorrectly thinking the device is not working, inadvertent early removal or a wet injection site. Some users have difficulty applying this hold force during the full drug delivery time. This can result in pain, discomfort, a wet injection site, early device removal and partial drug delivery.

SUMMARY

According to a first aspect, an injection device comprises:
a housing;
a needle shroud movable within the housing between an extended position and a retracted position; and
a needle shroud latch configured to hold the needle shroud in its retracted position,
wherein the needle shroud latch comprises a button arranged at the housing such that a user can actuate the button by applying an actuation force to the button to hold the needle shroud in its retracted position.

The button may be configured to be actuated by the user from an initial configuration, in which the needle shroud is able to move from its retracted position to its extended position, to an engaged configuration, in which the button holds the needle shroud in its retracted position, and the button maybe biased from its engaged configuration to its initial configuration.

The button may comprise an engaging element, wherein the needle shroud latch may comprise a cooperating element arranged at the needle shroud, and wherein the engaging element and the cooperating element may be configured such that actuation of the button by the user applying the actuation force to the button causes the engaging element to engage the cooperating portion to hold the needle shroud in its retracted position.

At least one of the engaging element and the cooperating element may have a bevelled surface.

The button may comprise a flap integrally formed with the housing.

The needle shroud may comprise a slot, and the needle shroud may be configured to be held in its retracted position due to engagement between a proximal-facing edge or surface of the flap and a distal-facing surface of the slot.

The button may comprise an actuation element and an arm projecting from the actuation element, wherein the arm may be configured to couple the button to the housing, wherein the actuation element may comprise an outer surface configured to pressed by a finger of the user to apply the actuation force, and wherein the arm and the actuation element may be resiliently coupled such that application of the actuation force to the outer surface of the actuation element causes the actuation element to pivot with respect to the arm such that it is deflected inwards towards the needle shroud, to hold the needle shroud in its retracted position.

The needle shroud latch may further comprise a latch clip coupled to the needle shroud and a cooperating element arranged at a collar of the injection device, and wherein the button, the latch clip and the cooperating element may be arranged such that user actuation of the button causes the button to engage the latch clip, which in turn may be caused to engage the cooperating element to hold the needle shroud in the retracted position.

The latch clip may be biased out of engagement with the cooperating element.

The latch clip may be integrally formed with the needle shroud.

The latch clip may comprise an arm extending from the needle shroud and at least one latch projection formed at a free end of the arm, wherein the latch clip may be configured such that engagement of the button with the latch clip due to user actuation of the button causes the arm to be deflected towards the collars such that the at least one latch projection engages the cooperating element to hold the needle shroud in the retracted position.

The latch clip may extend from a proximal end of the needle shroud in a proximal direction, substantially parallel to a longitudinal axis of the injection device.

The cooperating element may comprise a slot formed at an outer surface of the collar, wherein the slot may be configured to be engaged by the latch clip to hold the needle shroud in its retracted position.

In some examples, the slot is a recess or an aperture.

The latch clip may comprise an arm extending from the needle shroud and at least one latch projection formed at a free end of the arm, the cooperating element may comprise a slot formed at an outer surface of the collar, and the latch clip may be configured such that engagement of the button with the latch clip due to user actuation of the button causes the arm to be deflected towards the collar such that the at least one latch projection engages the slot to hold the needle shroud in the retracted position.

The slot may be a recess or an aperture.

A distal-facing surface of the at least one latch projection may be arranged to engage a respective proximal-facing surface of the slot when the latch clip is deflected towards the collar.

The distal-facing surface may be bevelled.

The proximal-facing surface may be bevelled.

The injection device may comprise a medicament delivery mechanism.

The medicament delivery device may comprise a plunger and a drive spring for applying a biasing force to the plunger.

The medicament delivery mechanism may be configured to be activated in response to retraction of the needle shroud into its retracted position.

The button may be arranged at an outer surface of the housing and/or at a proximal end of the housing.

The injection device may further comprise a control spring configured to apply a biasing force to bias the needle shroud from its retracted position to its extended position.

In some examples, the control spring does not exert the biasing force on an injection site when the needle shroud is pressed against the injection site and held in its retracted position by the latch.

The injection device may further comprise a reservoir containing a medicament.

According to a second aspect, a method for holding a needle shroud of an injection device during medicament delivery is disclosed. The method comprises:

moving the needle shroud within a housing of the injection device from an extended position to a retracted position;
  subsequent to moving the needle shroud within a housing of the injection device from the extended position to the retracted position, and while the needle shroud is in the retracted position, using a needle shroud latch of the injection device to hold the needle shroud in its retracted position,
  wherein the needle shroud latch comprises a button arranged at the housing such that a user can actuate the button, and
  wherein using the needle shroud latch to hold the needle shroud in its retracted position comprises actuating the button to hold the needle shroud in its retracted position.

The method may further comprise releasing the needle shroud latch to release the needle shroud.

The method may further comprise, subsequent to releasing the needle shroud latch, moving the needle shroud from its retracted position to its extended position.

The method may further comprise dispensing medicament from a syringe of the injection device.

BRIEF DESCRIPTION OF THE DRAWINGS

Exemplary embodiments are described with reference to the accompanying drawings, in which:

FIG. 6C shows a cross-sectional of the injection device of FIG. 6B in the activated state, with the needle shroud in the retracted position and the button in an engaged configuration;

FIG. 6D shows a cross-sectional of the injection device of FIG. 6C in a post-use state, with the needle shroud in the retracted position and the button in the initial configuration;

DETAILED DESCRIPTION

Figure 1:
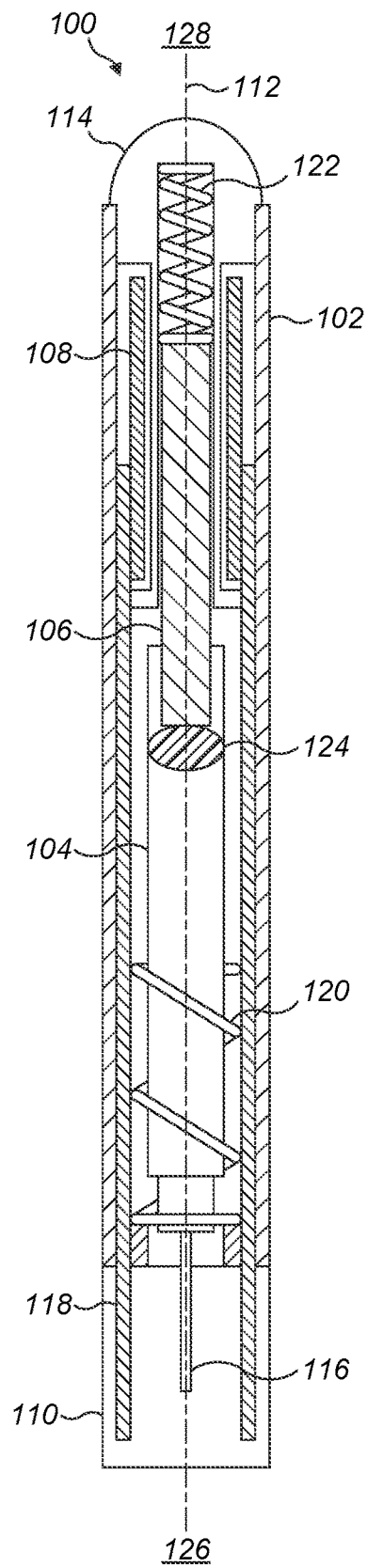
FIG. 1 shows a schematic example of a cross section of an injection device in accordance with one or more aspects of the present disclosure.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence medicament delivery. One of these actions may involve a user placing a needle shroud (also referred to as a needle cover or needle sleeve) against an injection site of a subject and applying an axial force to the device to cause the needle shroud to retract into the housing of the device. As the needle shroud retracts into the housing, the needle of the device extends beyond the needle shroud and penetrates the injection site of the subject (e.g. the subject's skin). Medicament delivery may be automatically initiated in response to the retraction of the needle shroud or in response to some other action by the user, for example the user pressing a button on the device. Once medicament delivery has been initiated, a medicament delivery mechanism will cause medicament contained within the device to be injected into the subject via the needle. The user should hold the device steady with respect to the injection site during the course of medicament delivery to ensure the needle remains steady within the subject. This is to minimize pain and/or discomfort for the subject, and to prevent a wet injection site, early device removal and/or partial medicament delivery.

After the device is removed from injection site, many autoinjectors cover the needle with the needle shroud/needle cover, which is extended out of the device by a control spring. During activation of the device and while holding the device steady during medicament delivery, the user counteracts the biasing force applied by the control spring to the needle shroud. However, some users such as those with impaired dexterity may find it difficult to counteract the biasing force of the control spring, particularly if they are required to hold the device steady for a relatively long period of time during medicament delivery. It may be beneficial to provide a device which is easier to handle during medicament delivery.

Injection devices described herein use a needle shroud latch for holding a needle shroud in a retracted position during medicament delivery. The latch comprises a button configured to engage with the needle shroud to hold the needle shroud in its retracted position and prevent the needle shroud from extending. The button is actuated by a user while the needle shroud is in its retracted position, to engage with the needle shroud. In instances where the injection device comprises a control spring for biasing the needle shroud to extend out of the injection device body, engagement between the button and the needle shroud prevents a biasing force provided by the control spring to the needle shroud from being transferred to the injection site of the subject. As such, the user of the device may no longer need to counteract the biasing force of the control spring to hold the device steady against the injection site. The device may therefore be easier to handle during medicament delivery, for example by users with impaired dexterity.

FIG. 1 shows a schematic example of a cross section of an injection device 100 according to one or more aspects of the present disclosure. The injection device 100 is configured to inject a medicament into a subject. The injection device 100 comprises an outer casing 102 (also referred to as a housing or injection device body) that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. Typically a user removes cap 110 from the outer casing 102 before device 100 can be operated.

As shown, casing 102 is substantially cylindrical and has a substantially constant diameter along the longitudinal axis of the device 100. The injection device 100 has a distal region 126 and a proximal region 128. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle shroud 118 (also referred to as a "needle sleeve" or "needle cover") extend from a distal end of the outer casing 102. The retractable needle shroud 118 is biased axially in the distal direction of the injection device 100, for example using a control spring 120. The needle shroud 118 is coupled to the outer casing 102 to permit axial movement of needle shroud 118 relative to the outer casing 102. For example, the shroud 118 can move in a longitudinal direction parallel to longitudinal axis 112. Specifically, movement of shroud 118 in a proximal direction relative to the casing 102 can cause a needle 116 to extend from distal region of the casing 102, and outside a distal end of the shroud 118.

The plunger 106 is biased towards the distal end of the injection device 100 by a biasing means, for example comprising a drive spring 122. The plunger 106 is retained in an initial position by a combination of the rear casing 114 and the collar 108, preventing the biasing means from displacing the plunger 106 in the distal direction. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 124 in the reservoir 104, displacing the stopper 124 in the distal direction and causing medicament stored in the reservoir 104 to be expelled from the injection device 100 via the needle 116.

Activation of the injection device 100 can occur via several mechanisms. For example, the needle 116 may be fixedly located relative to the casing 102 and initially be located within an extended needle shroud 118. Proximal movement of the needle shroud 118 by placing a distal end of the shroud 118 against an injection site of the subject and moving the casing 102 in a distal direction will uncover the distal end of the needle 116. Such relative movement allows the distal end of the needle 116 to extend into the injection site. Such insertion is termed "manual" insertion as the needle 116 is manually inserted via the user's manual movement of the casing 102 relative to shroud 118. Retraction of the shroud 118 into the casing 102 causes the collar 108 to rotate, releasing the plunger 106.

Another form of activation is "automated", whereby the needle 116 moves relative to casing 102. Such insertion can be triggered by movement of the shroud 118 and/or by another form of activation, such as, for example, user actuation of a button of the injection device 100.

Typically, the user presses the needle shroud 118 against an injection site to push the needle shroud 118 at least partially into the device casing 102. The exposed needle 116 is pushed into the injection site of the subject. In a holding position, medicament is automatically dispensed from the needle 116 via an automated mechanism. A user typically holds the needle shroud 118 in the holding position for a predetermined period of time, to ensure that the correct dose of medicament is dispensed from the device 100, before removing the device 100 from the injection site.

The spring biasing force from the control spring 120 against which the user applies a force to move the needle shroud 118 is one component of an "activation force" of the device 100. The activation force refers to the force or force profile that the user exerts on the device 100 to move the needle shroud 118 from the extended position shown in FIG. 1 to a retracted position within the casing 102 for medicament delivery. If this force or force profile is not well balanced, it can lead to difficulty in activating the device 100 for some users, or increase the pain or anxiety associated with using the device 100.

Following injection, the needle 116 can be retracted within the shroud 118. Retraction can occur when the shroud 118 moves distally under the biasing of the control spring 120 as a user removes the device 100 from the injection site of the subject. Once a distal end of the shroud 118 has moved past a distal end of the needle 116 such that the needle 116 is covered, the shroud 118 may be locked in its extended position to prevent any (substantial) proximal movement of the shroud 118 relative to the casing 102 (i.e., preventing any movement of the shroud 118 that would uncover the needle 116). The shroud 118 may be locked by a needle shroud non-return element, such as a catch.

Figure 2A:
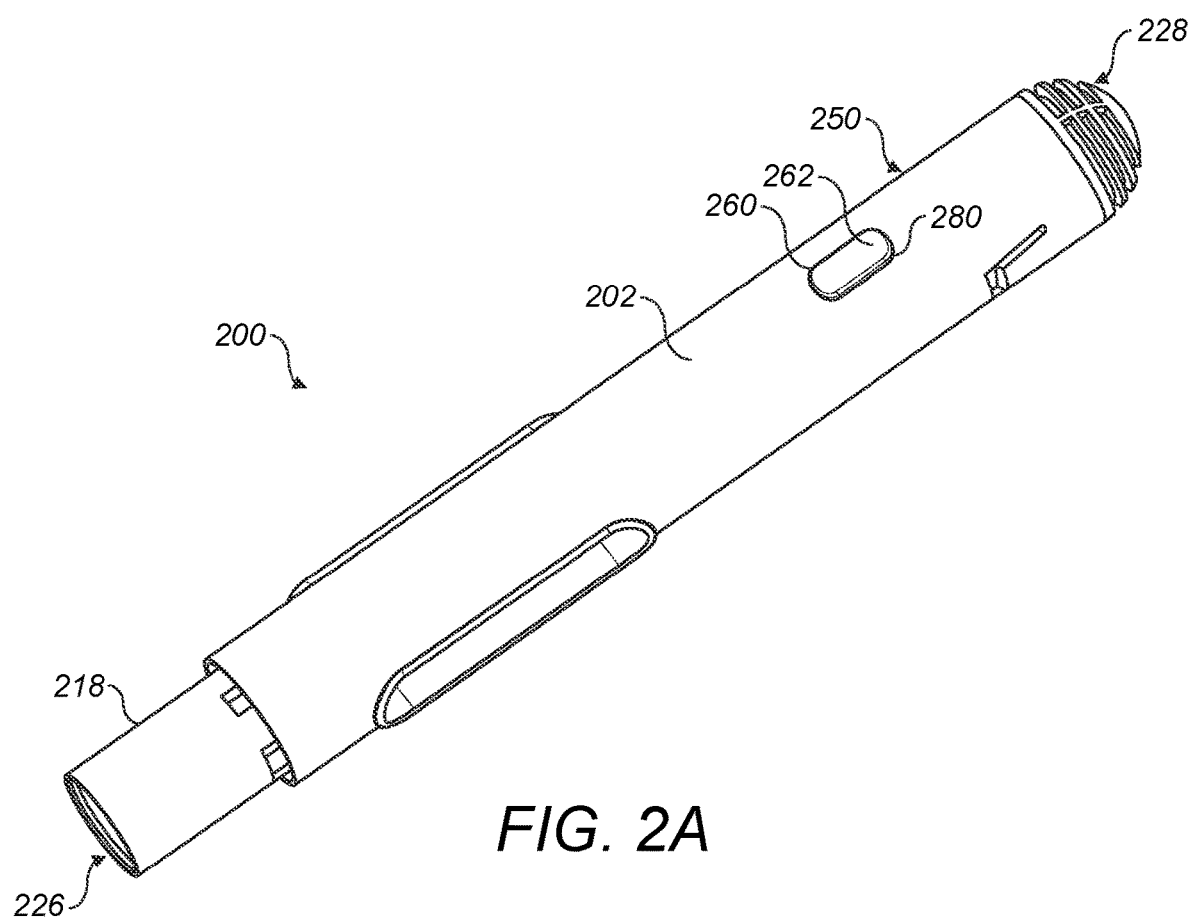
FIG. 2A shows an injection device according to a first embodiment of the present disclosure, in a pre-use state.

FIG. 2A shows an example of an injection device 200 in accordance with a first embodiment of the present disclosure. The injection device 200 may correspond to the injection device 100 of FIG. 1, having one or more features of the injection device 100 of FIG. 1.

The injection device 200 has a distal end 226 and a proximal end 228, and comprises a housing 202 (which may correspond to the casing 102 of FIG. 1). The housing 202 may be cylindrical and extend along the longitudinal axis of the injection device 200. FIG. 2A shows the injection device 200 in a pre-use state, in which a needle shroud 218, in an extended position relative to the housing 202, extends from a distal end of the housing 202 to cover a needle (e.g., needle 116 of FIG. 1). The needle shroud 218 can be moved from its extended position to its retracted position by a user placing a distal end of the needle shroud 218 against an injection site of a subject and applying a force to the housing 202 in a distal axial direction, causing the needle shroud 218 to move axially in a proximal direction with respect to the housing 202 and thereby retract into the housing 202 to expose the needle.

The injection device 200 may comprise a resilient member such as a control spring (e.g., control spring 120) for biasing the needle shroud 218 in a distal direction, from its retracted position towards its extended position. In such circumstances, the user must apply sufficient force to the housing 202 of the injection device 200 to counteract the biasing force exerted on the needle shroud 218 by the control spring so that the needle shroud 218 may be retracted. The user maintains a holding force while pressing the injection device 200 against the injection site until medicament delivery is complete. Counteracting the biasing force may be difficult for some users, for example users with dexterity issues, particularly where the user maintains a holding force for a long period of time during medicament delivery.

The injection device 200 comprises a needle shroud latch 250 for holding the needle shroud 218 in its retracted position relative to the housing 202. The latch 250 is actuated by a user while the needle shroud 218 is in its retracted state to prevent the needle shroud 218 from moving distally with respect to the housing 202 towards its extended position. By holding the needle shroud 218 in its retracted position, the biasing force applied to the needle shroud 218 by the control spring is no longer exerted on the injection site. As such, the user is no longer required to counteract the biasing force while holding the injection device 200 against the injection site.

As shown in FIG. 2A, the latch 250 comprises a button 260 arranged at an outer surface of the housing 202. The button 260 is arranged such that it can be actuated by a user to hold the needle shroud 218 in its retracted position. In this example the button 260 is arranged at the side of the injection device 200, at the proximal end 228 of the injection device 200, so that it may be easily actuated by a finger or thumb of the user. However, a different location of the button 260 may be envisaged.

Figure 2B:
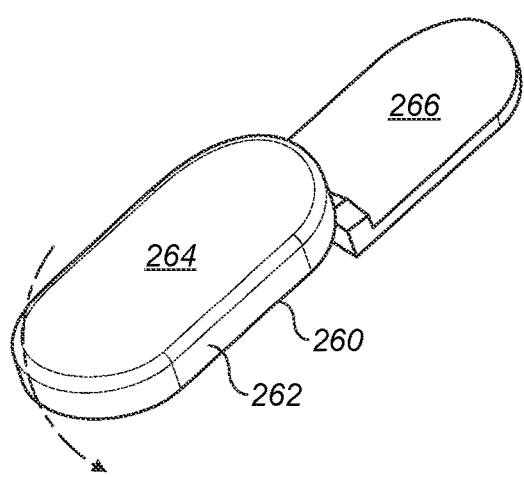
FIG. 2B shows a button of the injection device of FIG. 2A in greater detail.

FIG. 2B shows the button 260 of FIG. 2A in greater detail, with the other features of the injection device 200 hidden for clarity. The button 260 has a plate-like actuation element 262 and an arm 266 projecting from the actuation element 262 in an axial direction, in this example in a proximal axial direction. The actuation element 262 is configured to project through an aperture 280 in the housing 292 of the injection device 200 such that an outer surface 264 of the actuation element 262 may be actuated (e.g., pressed) by the user to actuate the button 260 for holding the needle shroud 218 in its retracted position. The arm 266 is configured to couple the button 260 to the housing 202.

At least a portion of the arm 266 and/or actuation element 262 may be resilient (i.e., the arm 266 and actuation element 262 are resiliently coupled) such that the actuation element 262 can be deflected relative to the arm 266 in response to the user pressing the outer surface 264 of the actuation element 262, as described later in relation to FIGS. 3A-D. At least a portion of the arm 266 and/or actuation element 262 may be formed from a resilient material to allow for the deflection of the actuation element 262. The actuation element 262 may have an engaging element 268 (shown in FIG. 3A) arranged at a lower surface of the actuation element 262 for engaging with the needle shroud 218 to hold the needle shroud 218 in its retracted position.

FIGS. 3A to 3D show a cross-section of the device 200 in a plane parallel to the longitudinal axis of the device 200, before and after activation of the device 200. Certain features of the device 200 may be omitted from FIGS. 3A to 3D for the sake of clarity. FIGS. 3A to 3D mainly show the proximal end 228 of the device 200, with features of the distal end 226 such as a needle omitted for clarity. FIGS. 3A to 3D also show one half of the device 200 about the longitudinal axis of the device 200.

Figure 3A:
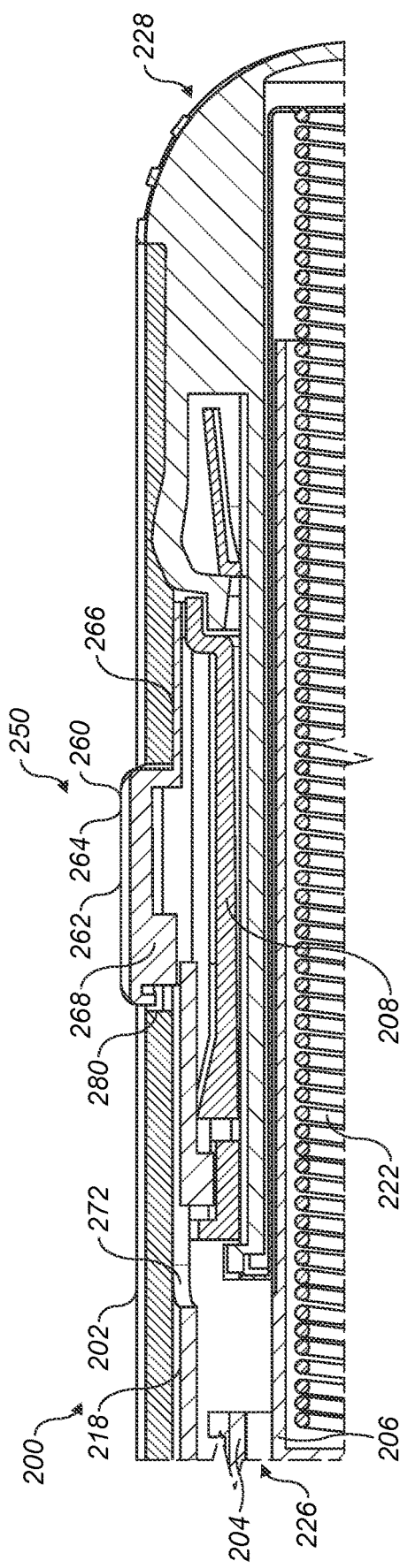
FIG. 3A shows a cross-sectional view of a portion of the injection device of FIG. 2A, in the pre-use state, with a needle shroud in an extended position and the button in an initial configuration.

The housing 202 contains a reservoir 204 that contains the medicament to be injected, wherein the reservoir 204 may, for example, be in the form of a syringe. A proximal end of the reservoir 204 is shown in FIG. 3A. The injection device 200 also contains a medicament delivery mechanism for ejecting medicament from the reservoir 204, via the needle. In this example, the medicament delivery mechanism comprises a plunger 206 and a biasing means for applying a biasing force to the plunger 206 to cause medicament to be expelled from the reservoir 204. In this example, the biasing means comprises a drive spring 222, however alternative forms of biasing means may be used instead, such as an electromechanical mechanism or a pressurized gas-driven mechanism.

FIG. 3A shows the device 200 in its initial, pre-use state. The needle shroud 218 of the injection device 200 is not currently being held by a user against an injection site. As such, the needle shroud 218 is in its initial, extended position with respect to the housing 202, in which a distal portion of the needle shroud 218 extends from a distal end of the housing 202 and surrounds a needle to protect the user and the subject (if the subject is different from the user) from the needle. The needle shroud 218 is biased into its extended position by a control spring, which applies a biasing force to the needle shroud 218 to hold the needle shroud 218 in its extended position.

As shown in FIG. 3A, the button 260 of the latch 250 is arranged at the housing 202. The actuation element 262 extends substantially parallel to the longitudinal axis of the injection device 200. The actuation element 262 is accessible to a user through the aperture 280 in the housing 202 such that the user is able to press the outer surface 264 of the actuation element 262. FIG. 3A shows the actuation element 262 extending through the aperture 280 such that a portion of the actuation element 262 comprising the outer surface 264 extends outside of the housing 202, beyond the outer surface of the housing 202. However, it should be understood that in other examples the actuation element 262 may not extend through the aperture 280, or may extend through the aperture 280 but not extend outside of the outer surface of the housing 202.

The arm 266 of the button 260 is retained within the housing 202 such that the button 260 is coupled to the housing 202. As shown in FIG. 3A, the arm 266 extends from a proximal end of the actuation element 262, inside the housing 202, and adjacent to the inner surface of the housing 202. FIG. 3A shows the arm 266 extending between the inner surface of the housing 202 and the collar 208 of the injection device 200, however other suitable locations of the arm 266 may be envisaged.

The engaging element 268 in this example comprises a protuberance that extends radially inwards from the lower surface of the actuation element 262, into the housing 202. The latch 250 further comprises a cooperating element configured to be engaged by the engaging element 268 to hold the needle shroud 218 in its retracted state. FIG. 3A shows the cooperating element taking the form of a slot 272 provided in the needle shroud 218, the slot 272 configured to be engaged by the engaging element 268 of the button 260 when the button 260 is actuated by a user. The slot 272 could be a recess or an aperture formed in the needle shroud 218, for example at a proximal end portion of the needle shroud 218. However, in other examples the cooperating element may take a different form, such as a protrusion or a friction surface.

FIG. 3A shows the button 260 in an initial configuration, in which the button 260 has not yet been actuated by the user and the engaging element 268 does not yet engage the cooperating element. The cooperating element is arranged on the needle shroud 218 such that, when the needle shroud 218 is in its extended position, the engaging element 268 is misaligned with the cooperating element and therefore cannot engage the cooperating element to hold the needle shroud 218. FIG. 3A shows that, when the needle shroud 218 is in its extended position, the engaging element 268 of the button 260 is adjacent to an outer surface of the needle shroud 218 such that actuation of the button 260 is inhibited by engagement between the engaging element 268 and the outer surface of the needle shroud 218.

To activate the injection device 200 shown in FIG. 3A for medicament delivery, the user grips the outer surface of the housing 202 and presses the distal end of the needle shroud 218 against the injection site of a subject (which may or may not be the user), applying a distal force to the injection device 200 such that the needle shroud 218 moves axially into the housing 202 in a proximal direction, into its retracted position. The distal force counteracts the biasing force exerted on the needle shroud 218 by the control spring.

Figure 3B:
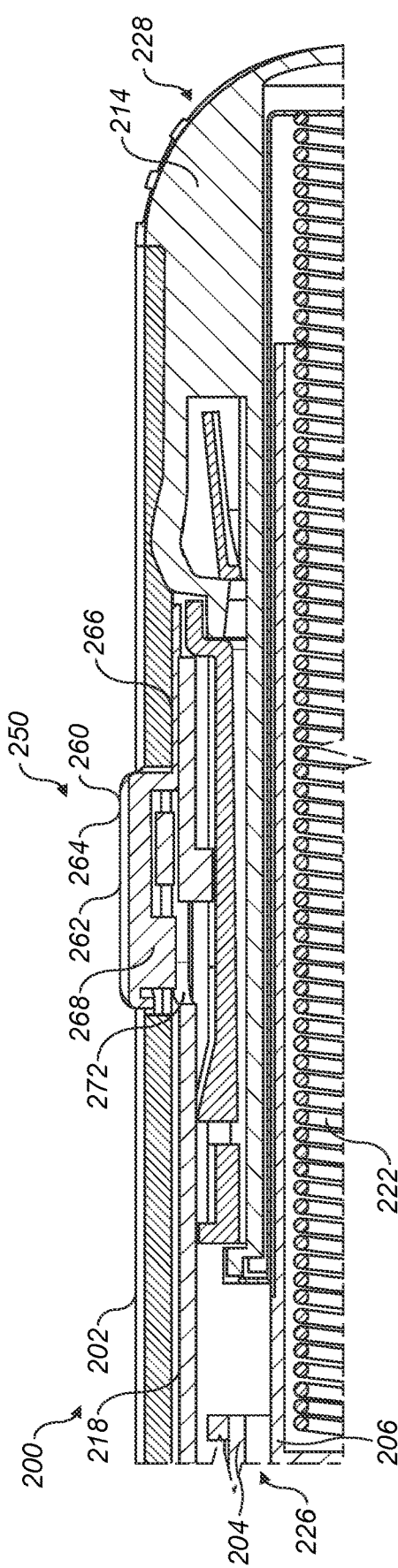
FIG. 3B shows a cross-sectional of the injection device of FIG. 3A in an activated state, with the needle shroud in a retracted position and the button in the initial configuration.

FIG. 3B shows the injection device 200 of FIG. 3A now in its activated state, with the needle shroud 218 having moved proximally within the housing 202 into its retracted position. Proximal movement of the needle shroud 218 relative to the needle has uncovered the distal end of the needle, allowing the distal end of the needle to penetrate and extend into the injection site. Proximal movement of the needle shroud 218 has also brought the cooperating element (in this case, the slot 272) into alignment with the engaging element 268 of the button 260 such that the cooperating element and the engaging element 268 are aligned when the needle shroud 218 is in its retracted position. However, FIG. 3B shows that the button 260 remains in its initial configuration and therefore the engaging element 268 does not yet engage the cooperating element of the needle shroud 218. If the user were to remove the needle shroud 218 from the injection site at this stage, the needle shroud 218 would be free to move in a distal direction under the biasing force of the control spring, from its retracted position back to its extended position. The user therefore applies a holding force to the housing 202 of the injection device 200 to counteract the biasing force and maintain the needle shroud 218 in its retracted position.

Medicament delivery by the medicament delivery mechanism of the injection device 200 may be activated automatically, for example in response to the retraction of the needle shroud 218 (e.g., in response to retraction of the needle shroud 218 into its retracted position). The plunger 206 within the housing 202 of the injection device 200 may be biased towards the distal end of the injection device 200 by the biasing means, in this example comprising the drive spring 222. The plunger 206 is retained in an initial position by a combination of the rear casing 214 and the collar 208 (which may correspond to the rear casing 114 and collar 108 of FIG. 1), preventing the biasing means from displacing the plunger 206 in the distal direction. Retraction of the needle shroud 218 into the housing 202 causes the collar 208 to rotate due to an engagement between the needle shroud 218 and the collar 208, releasing the plunger 206. Once the plunger 206 has been released, the biasing means causes the plunger 206 to move in the distal direction (i.e., towards the needle end of the injection device 200) by exerting a force on the plunger 206. The plunger 206 contacts a stopper (e.g., stopper 124 of FIG. 1) in the reservoir 204, displacing the stopper in the distal direction and causing medicament stored in the reservoir 204 to be expelled from the injection device 100 via the needle as the plunger 206 moves distally.

The user should hold the injection device 200 in a fixed position with respect to the injection site during medicament delivery until delivery is complete, maintaining their holding force to counteract the biasing force of the control spring. However, certain users such as those with impaired dexterity may have difficulty in holding the injection device 200 steady. For example, the user may have difficulty in maintaining sufficient holding force to keep the needle shroud 218 in its retracted position, particularly when the holding force is applied for a substantial length of time. If the user does not hold the injection device 200 steady, there may be a risk of pain or discomfort for the subject receiving the injection, medicament leakage from the injection site, and/or incomplete medicament delivery. By using the latch 250 of the injection device 200, one or more of these issues may be addressed.

Figure 3C:
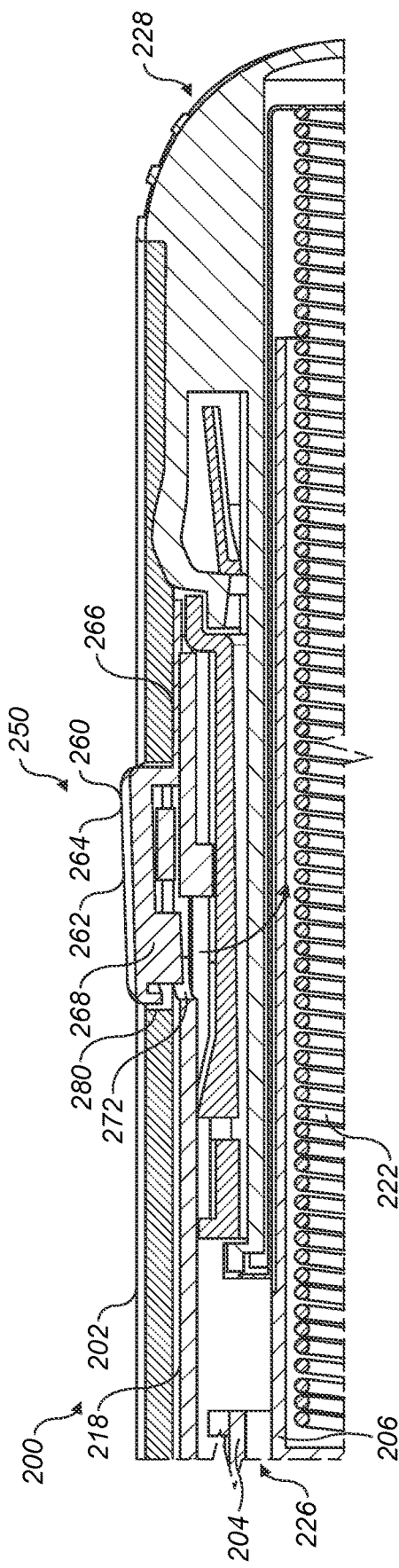
FIG. 3C shows a cross-sectional of the injection device of FIG. 3B in the activated state, with the needle shroud in the retracted position and the button in an engaged configuration.

FIG. 3C shows the injection device 200 of FIG. 3B after the user has actuated the latch 250 to hold the needle shroud 218 in its retracted position during medicament delivery. The user has actuated the latch 250 by applying an actuation force to the button 260 to move it from its initial configuration to an engaged configuration, to cause the button 260 to engage the needle shroud 218. For example, the user has applied the actuation force to the outer surface 264 of the actuation element 262 by pressing a finger or thumb directly against the outer surface 264 to push the actuation element 262 radially inwards and into the housing 202, causing the engaging element 268 to engage the cooperating element (e.g., slot 272). As the actuation force is applied to the actuation element 262, the actuation element 262 is deflected such that it pivots with respect to the arm 266 due to the resilient coupling between the actuation element 262 and arm 266, pivoting towards the needle shroud 218 about an axis perpendicular to the longitudinal axis of the injection device 200.

FIG. 3C shows the engaging element 268 (in this example, a protuberance extending radially inward from the actuation element 262) engaging the cooperating element (in this example, the slot 272). Since the button 260 is prevented from moving axially due to the coupling between the button 260 and the housing 202, engagement between the engaging element 268 and the cooperating element prevents the needle shroud 218 from moving axially (at least distally, and optionally proximally) to hold the needle shroud 218 in its retracted position.

Since the needle shroud 218 is held in its retracted position by the button 260, the biasing force exerted by the control spring on the needle shroud 218 to bias the needle shroud 218 towards its extended position may no longer be transferred by the needle shroud 218 to the injection site. As such, the user may no longer be required to counteract the biasing force of the control spring with a sufficient holding force to hold the injection device 200 steady against the injection site during medicament delivery. The user may find the injection device 200 easier to handle during medicament delivery, which may reduce the risk of pain or discomfort being experienced by the subject receiving the injection, reduce the risk of medicament leakage from the injection site, and/or reduce the risk of incomplete medicament delivery. The reduction in the required holding force may be advantageous for users with impaired dexterity. The safety of the injection device 200 may be increased compared to one or more prior art devices.

The engaging element 268 and the cooperating element may be dimensioned such that axial movement of needle shroud 218 is minimized when the engaging element 268 and the cooperating element are engaged. For example, where the cooperating element comprises a slot 272, the slot 272 may be configured to have a shape (e.g., cross-section) that closely corresponds to the shape (e.g., cross-section) of the engaging element 268. As an example, a width of the slot 272 substantially parallel to the longitudinal axis of the injection device 200 may closely correspond to a width of the engaging element 268 substantially parallel to the longitudinal axis of the injection device 200 (when the button 260 is in its engaged configuration). The shape (e.g., cross-section and/or width) of the slot 272 may be slightly greater than the corresponding shape (e.g., cross-section and/or width) of the engaging element 268 to provide tolerance for insertion of the engaging element 268 into the slot 272.

Where the cooperating element comprises a slot 272, the needle shroud 218 may be held in its retracted position (i.e., prevented from moving distally) due to engagement between a proximal-facing surface of the engaging element 268 (e.g., a proximal-facing surface of the protuberance) and a distal-facing surface of the slot 272.

Figure 3D:
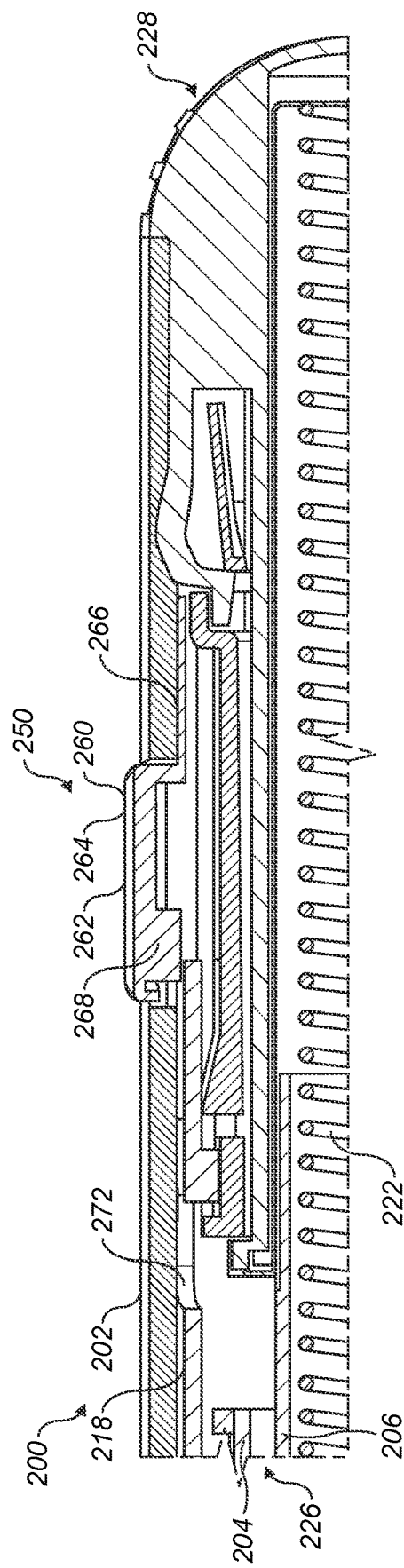
FIG. 3D shows a cross-sectional of the injection device of FIG. 3C in a post-use state, with the needle shroud in the extended position and the button in the initial configuration.

Once medicament delivery is complete, the latch 250 may be moved from its engaged configuration back to its initial configuration such that the needle shroud 218 is no longer held by the latch 250 and is free to move distally towards its extended position. FIG. 3D shows the injection device 200 of FIG. 3C in its post-use state, after medicament delivery has been completed and the latch 250 has moved to its initial configuration.

The latch 250 may be biased by a latch biasing mechanism from its engaged configuration to its initial configuration. For example, in the injection device 200 shown in FIG. 3D, the resilient portion of the button 260 (e.g., the resilient arm 266) acts as a latch biasing mechanism, biasing the button 260 from its engaged configuration to its initial configuration. Due to the presence of the latch biasing mechanism, the user may move the button 260 back to its initial state by removing the actuation force applied to the actuation element 262, with the actuation element 262 automatically pivoting back to its initial position and causing the engaging element 268 to be disengaged from the cooperating element (e.g., slot 272) as the actuation force is reduced. FIG. 3D shows the button 260 having returned to its initial configuration. Since the engaging element 268 is no longer engaged with the cooperating element, the needle shroud 218 is no longer held in its retracted position and is free to move distally towards its extended state.

As the user removes the injection device 200 from the injection site, the needle shroud 218 moves distally with respect to the housing 202 until it reaches its extended position, covering the needle. In some examples, the injection device 200 may comprise a needle shroud catch that prevents proximal movement of the needle shroud 218 to expose the needle, after the needle shroud 218 has moved distally to cover the needle. The needle shroud catch may be manually or automatically activated, and may increase the safety of the device.

Figure 4:
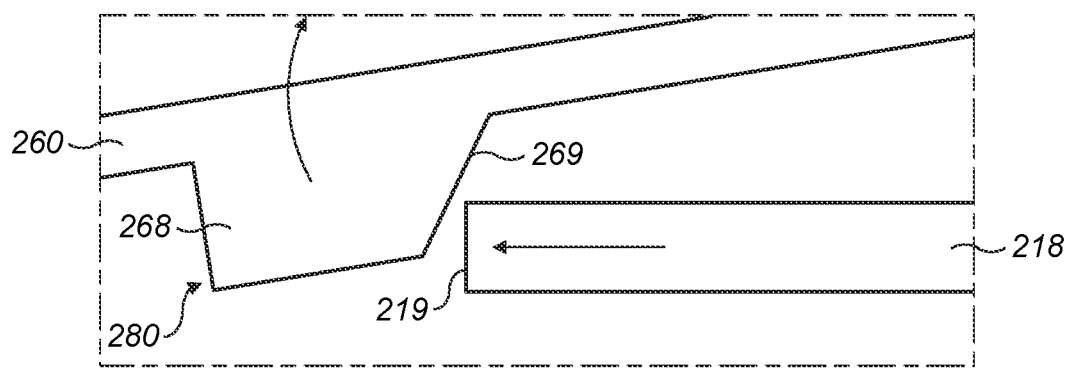
FIG. 4 shows a close-up portion of the button and needle shroud of FIG. 3C, in which an engaging element of the button has a proximal-facing surface that is beveled.

In some examples, the proximal-facing surface of the engaging element 268 and/or the distal-facing surface of the cooperating element may be bevelled such that distal movement of the needle shroud 218 from its retracted position causes the button 260 (e.g., actuating element 262) to pivot radially outwards towards its initial configuration. FIG. 4 shows a close-up portion of the button 260 and needle shroud 218 of FIG. 3C in which the engaging element 268 has a proximal-facing surface 269 that is bevelled (i.e., sloped inwardly such that the proximal-facing surface 269 faces both the proximal end 228 of the injection device 200 and the longitudinal axis of the injection device 200). The proximal-facing surface 269 is bevelled such that, once a user removes the actuation force from the button 260 and the needle shroud 218 moves distally under the biasing force of the control spring, a distal-facing surface 219 of the cooperating element (in this example, the cooperating element comprising a slot 272) engages the proximal-facing surface 269. Distal movement of the needle shroud 218 causes the distal-facing surface 219 to apply a force to the proximal-facing surface 269 which, due to the bevel, urges the engaging element 268 radially outwards and out of engagement with the cooperating element. The provision of the bevel may therefore assist with automatic movement of the button 260 back to its initial configuration, in addition to reducing the risk of the engaging element 268 becoming stuck in engagement with the needle shield 218 under the biasing force of the control spring. While FIG. 4 shows the proximal-facing surface 269 of the engaging element 268 being bevelled and the distal-facing surface 219 of the cooperating element being square, it should be understood that in other examples the proximal-facing surface 269 of the engaging element 268 may be square and the distal-facing surface 219 of the cooperating element may be bevelled, or both the proximal-facing surface 269 of the engaging element 268 and the distal-facing surface 219 of the cooperating element may be bevelled.

While the injection device 200 described in relation to FIGS. 2A to 2B and FIGS. 3A to 3D has been described as having a particular medicament delivery mechanism, it should be understood that other suitable forms of medicament delivery mechanism may be used instead, for example as described previously. Furthermore, while it has been described in relation to FIGS. 2A to 2B and FIGS. 3A to 3D that the injection device 200 is activated to initiate medicament delivery in response to distal movement of the needle shroud 218, it should be understood that other mechanisms (automatic or manual) for initiating medicament delivery may be used in addition or alternatively, for example as described previously.

While the injection device 200 described in relation to FIGS. 2A to 2B and FIGS. 3A to 3D shows the arm 266 of the button 260 arranged proximal to the actuation element 262, it should be understood that in other examples the arm 266 and the actuation element 262 may be arranged in a different manner, for example with the arm 266 extending from a distal side of the actuation element 262 in a distal direction. Actuation of the button 260 would therefore cause the actuation element 262 to pivot inwardly towards the distal end 226 of the injection device 200, rather than the proximal end 228.

Figure 5:
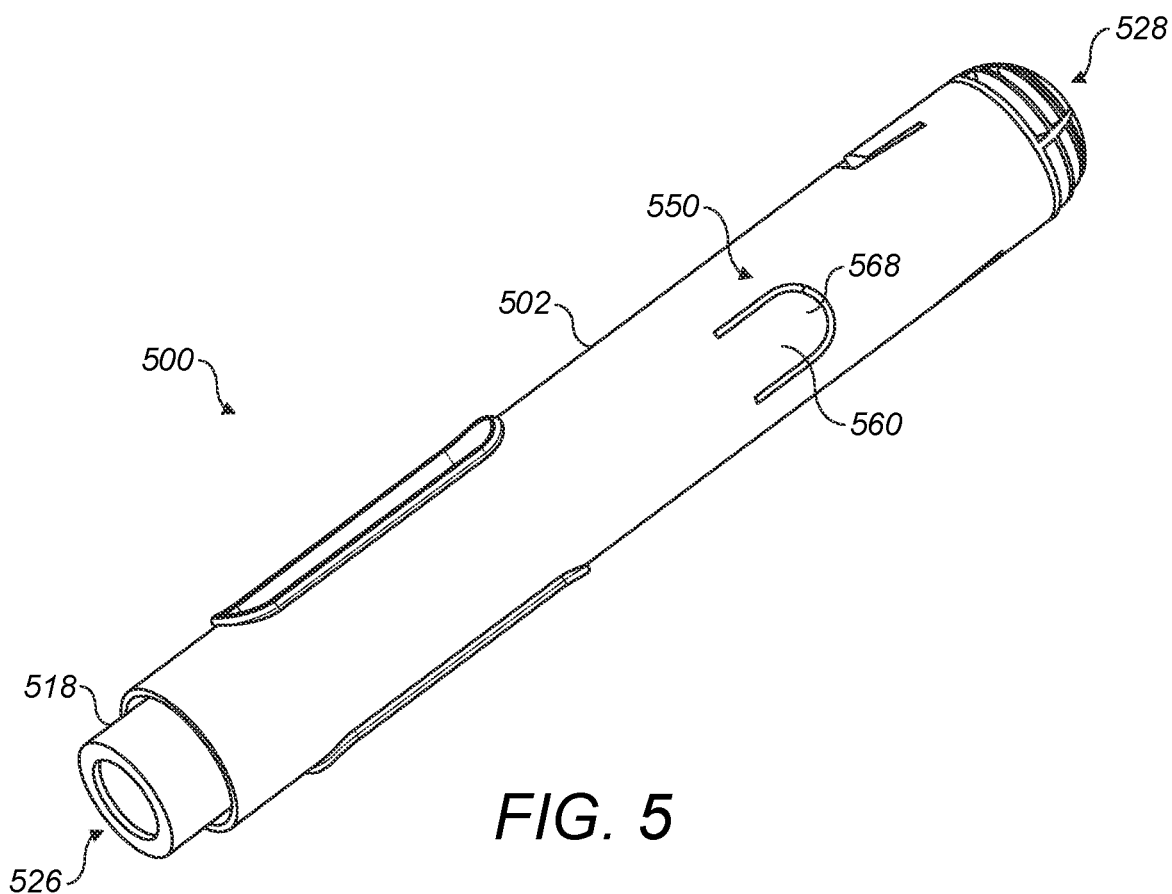
FIG. 5 shows an injection device according to a second embodiment of the present disclosure, in a pre-use state.

FIG. 5 shows an example of an injection device 500 in accordance with a second embodiment of the present disclosure. The injection device 500 may correspond to the injection device 100 of FIG. 1, having one or more features of the injection device 100 of FIG. 1. The injection device 500 is similar to the injection device 200 previously described in relation to FIGS. 2A to 2B and FIGS. 4A to 4D, however the latch 550 of the injection device 500 takes a different form to the latch 200 of the injection device 200.

The injection device 500 has a distal end 526 and a proximal end 528, and comprises a housing 502 (which may correspond to the casing 102 of FIG. 1). The housing 502 may be cylindrical and extend along the longitudinal axis of the injection device 500. FIG. 5 shows the injection device 500 in a pre-use state, in which a needle shroud 518, in an extended position relative to the housing 502, extends from a distal end of the housing 502 to cover a needle (e.g., needle 116 of FIG. 1). The needle shroud 518 can be moved from its extended position to its retracted position by a user placing a distal end of the needle shroud 518 against an injection site of a subject and applying a force to the housing 502 in a distal axial direction, causing the needle shroud 518 to move axially in a proximal direction with respect to the housing 502 and thereby retract into the housing 502 to expose the needle.

The injection device 500 may comprise a resilient member such as a control spring (e.g., control spring 120) for biasing the needle shroud 518 in a distal direction, from its retracted position towards its extended position. In such circumstances, the user must apply sufficient force to the housing 502 of the injection device 500 to counteract the biasing force exerted on the needle shroud 518 by the control spring so that the needle shroud 518 may be retracted. The user maintains a holding force while pressing the injection device 500 against the injection site until medicament delivery is complete. Counteracting the biasing force may be difficult for some users, for example users with dexterity issues, particularly where the user maintains a holding force for a long period of time during medicament delivery.

The injection device 500 comprises a needle shroud latch 550 for holding the needle shroud 518 in its retracted position relative to the housing 502. The latch 550 is actuated by a user while the needle shroud 518 is in its retracted state to prevent the needle shroud 518 from moving distally with respect to the housing 502 towards its extended position. By holding the needle shroud 518 in its retracted position, the biasing force applied to the needle shroud 518 by the control spring is no longer exerted on the injection site. As such, the user is no longer required to counteract the biasing force while holding the injection device 500 against the injection site.

As shown in FIG. 5, the latch 550 comprises a button. In the second embodiment, the button and the housing 502 are integrally formed. The button may comprise a cutout of the housing 502 in the form of a flap 560, the flap 560 integrally formed with the remainder of the housing 502 at one end of the flap 560 (e.g., a distal end, as shown in FIG. 5). The flap 560 is arranged such that it can be actuated by a user to hold the needle shroud 518 in its retracted position. In this example, the flap 560 is arranged at the side of the injection device 500, at the proximal end 528 of the injection device 500, so that it may be easily actuated by a finger or thumb of the user. However, a different location of the flap 560 may be envisaged.

An outer surface of the flap 560 may be pressed by the user to actuate the flap 560 for holding the needle shroud 518 in its retracted position.

At least a portion of the flap 560 may be resilient such that the flap 560 can be deflected radially inwards in response to the user pressing the outer surface of the flap 560 radially inwards, as described later in relation to FIGS. 6A-D. At least a portion of the flap 560 may be formed from a resilient material to allow for the deflection of the flap 560. An end portion of the flap 560 (which may be a proximal end portion and which may be opposite the end of the flap 560 connected to the remainder of the housing 502) may act as an engaging element 568 for engaging with the needle shroud 518 to hold the needle shroud 518 in its retracted position.

FIGS. 6A to 6D show a cross-section of the device 500 in a plane parallel to the longitudinal axis of the device 500, before and after activation of the device 500. Certain features of the device 500 may be omitted from FIGS. 6A to 6D for the sake of clarity. FIGS. 6A to 6D mainly show the proximal end 528 of the device 500, with features of the distal end 526 such as a needle omitted for clarity. FIGS. 6A to 6D also show one half of the device 500 about the longitudinal axis of the device 500.

Figure 6A:
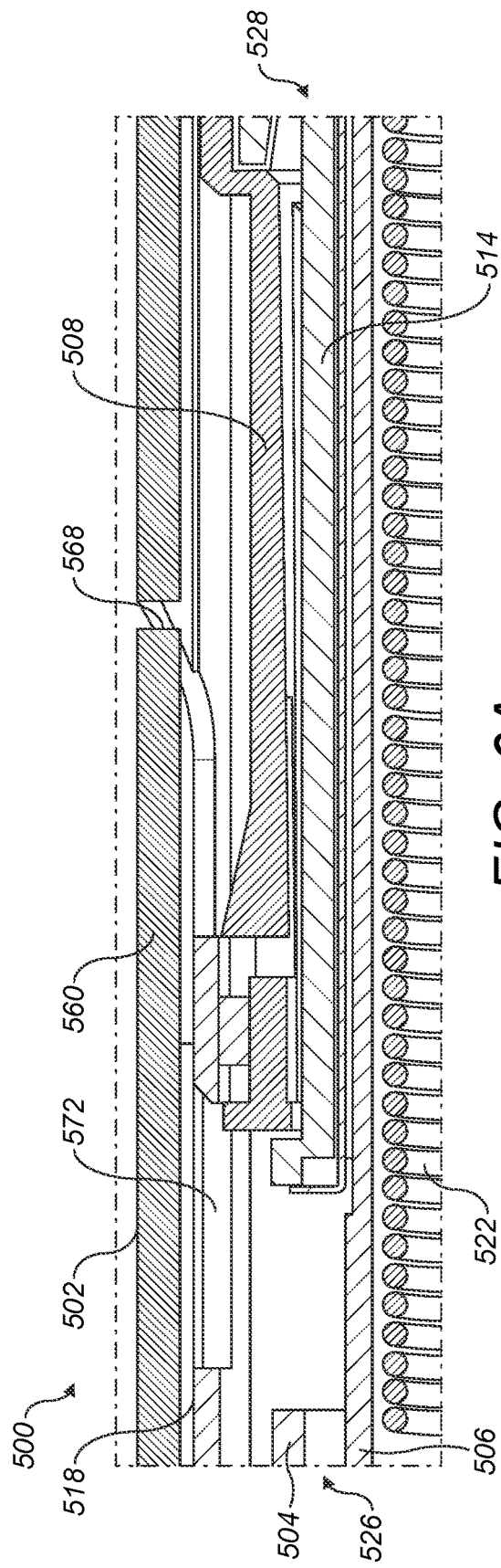
FIG. 6A shows a cross-sectional view of a portion of the injection device of FIG. 5, in the pre-use state, with a needle shroud in an extended position and the button in an initial configuration.

The housing 502 contains a reservoir 504 that contains the medicament to be injected, wherein the reservoir 504 may, for example, be in the form of a syringe. A proximal end of the reservoir 504 is shown in FIG. 6A. The injection device 500 also contains a medicament delivery mechanism for ejecting medicament from the reservoir 504, via the needle. In this example, the medicament delivery mechanism comprises a plunger 506 and a biasing means for applying a biasing force to the plunger 506 to cause medicament to be expelled from the reservoir 504. In this example, the biasing means comprises a drive spring 522, however alternative forms of biasing means may be used instead, such as an electromechanical mechanism or a pressurized gas-driven mechanism.

FIG. 6A shows the device 500 in its initial, pre-use state. The needle shroud 518 of the injection device 500 is not currently being held by a user against an injection site. As such, the needle shroud 518 is in its initial, extended position with respect to the housing 502, in which a distal portion of the needle shroud 518 extends from a distal end of the housing 502 and surrounds a needle to protect the user and the subject (if the subject is different from the user) from the needle. The needle shroud 518 is biased into its extended position by a control spring, which applies a biasing force to the needle shroud 518 to hold the needle shroud 518 in its extended position.

As shown in FIG. 6A, the flap 560 extends substantially parallel to the longitudinal axis of the injection device 500 at the housing 202 and is substantially flush with the outer surface of the remainder of the housing 502. The flap 560 is arranged such that the user is able to press the outer surface of the flap 560 to cause the flap 560 to pivot radially inwards, in some examples through an aperture in the housing 502.

The latch 550 further comprises a cooperating element configured to be engaged by the flap 560 to hold the needle shroud 518 in its retracted state. FIG. 6A shows the cooperating element taking the form of a slot 572 provided in the needle shroud 518, the slot 572 configured to be engaged by the engaging element 568 of the flap 560 when the flap 560 is actuated by a user. The slot 572 could be a recess or an aperture formed in the needle shroud 518, for example at a proximal end portion of the needle shroud 518. However, in other examples the cooperating element may take a different form, such as a protrusion or a friction surface.

FIG. 6A shows the flap 560 in an initial configuration, in which the flap 560 has not yet been actuated by the user and the engaging element 568 does not yet engage the cooperating element. The cooperating element is arranged on the needle shroud 518 such that, when the needle shroud 518 is in its extended position, the engaging element 568 is misaligned with the cooperating element and therefore cannot engage the cooperating element to hold the needle shroud 518.

To activate the injection device 500 shown in FIG. 6A for medicament delivery, the user grips the outer surface of the housing 502 and presses the distal end of the needle shroud 518 against the injection site of a subject (which may or may not be the user), applying a distal force to the injection device 500 such that the needle shroud 518 moves axially into the housing 502 in a proximal direction, into its retracted position. The distal force counteracts the biasing force exerted on the needle shroud 518 by the control spring.

Figure 6B:
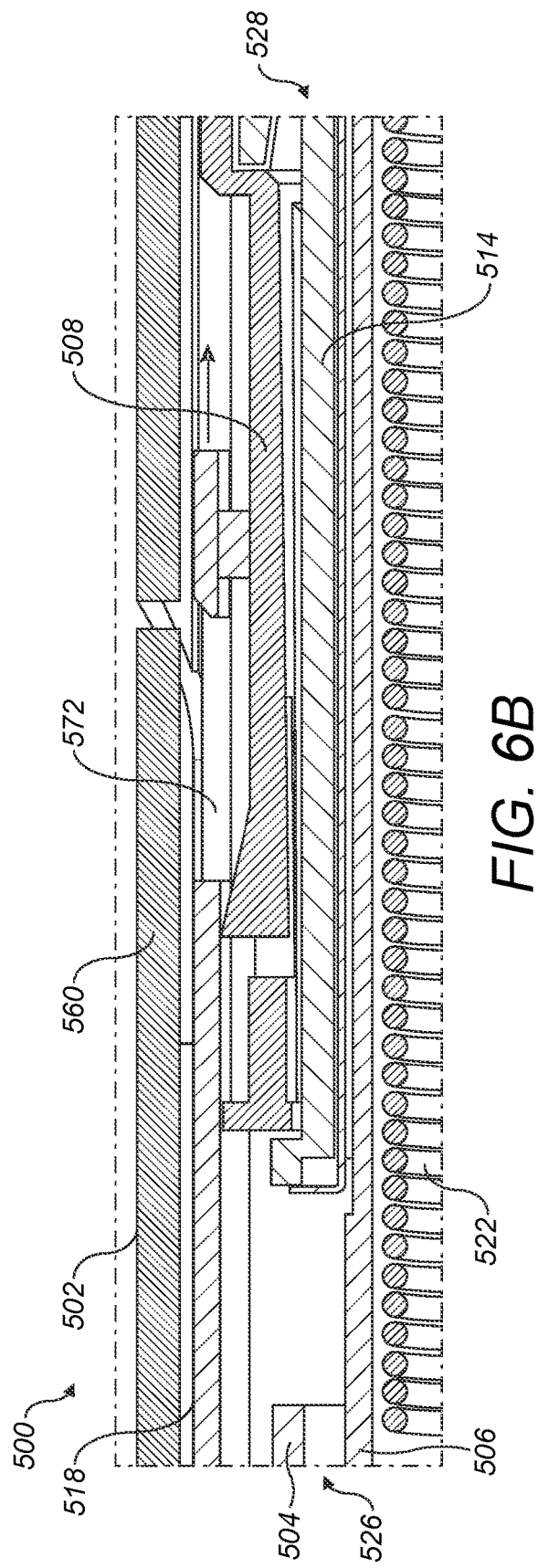
FIG. 6B shows a cross-sectional of the injection device of FIG. 6A in an activated state, with the needle shroud in a retracted position and the button in the initial configuration.

FIG. 6B shows the injection device 500 of FIG. 6A now in its activated state, with the needle shroud 518 having moved proximally within the housing 502 into its retracted position. Proximal movement of the needle shroud 518 relative to the needle has uncovered the distal end of the needle, allowing the distal end of the needle to penetrate and extend into the injection site. Proximal movement of the needle shroud 518 has also brought the cooperating element (in this case, the slot 572) into alignment with the engaging element 568 of the flap 560 such that the cooperating element and the engaging element 568 are aligned when the needle shroud 518 is in its retracted position. However, FIG. 6B shows that the flap 560 remains in its initial configuration and therefore the engaging element 568 does not yet engage the cooperating element of the needle shroud 518. If the user were to remove the needle shroud 518 from the injection site at this stage, the needle shroud 518 would be free to move in a distal direction under the biasing force of the control spring, from its retracted position back to its extended position. The user therefore applies a holding force to the housing 502 of the injection device 500 to counteract the biasing force and maintain the needle shroud 518 in its retracted position.

Medicament delivery by the medicament delivery mechanism of the injection device 500 may be activated automatically, for example in response to the retraction of the needle shroud 518 (e.g., in response to retraction of the needle shroud 518 into its retracted position). The plunger 506 within the housing 502 of the injection device 500 may be biased towards the distal end of the injection device 500 by the biasing means, in this example comprising the drive spring 522. The plunger 506 is retained in an initial position by a combination of the rear casing 514 and the collar 508 (which may correspond to the rear casing 114 and collar 108 of FIG. 1), preventing the biasing means from displacing the plunger 506 in the distal direction. Retraction of the needle shroud 518 into the housing 502 causes the collar 508 to rotate due to an engagement between the needle shroud 518 and the collar 508, releasing the plunger 506. Once the plunger 506 has been released, the biasing means causes the plunger 506 to move in the distal direction (i.e., towards the needle end of the injection device 500) by exerting a force on the plunger 506. The plunger 506 contacts a stopper (e.g., stopper 124 of FIG. 1) in the reservoir 504, displacing the stopper in the distal direction and causing medicament stored in the reservoir 504 to be expelled from the injection device 500 via the needle as the plunger 506 moves distally.

The user should hold the injection device 500 in a fixed position with respect to the injection site during medicament delivery until delivery is complete, maintaining their holding force to counteract the biasing force of the control spring. However, certain users such as those with impaired dexterity may have difficulty in holding the injection device 500 steady. For example, the user may have difficulty in maintaining sufficient holding force to keep the needle shroud 518 in its retracted position, particularly when the holding force is applied for a substantial length of time. If the user does not hold the injection device 500 steady, there may be a risk of pain or discomfort for the subject receiving the injection, medicament leakage from the injection site, and/or incomplete medicament delivery. By using the latch 550 of the injection device 500, one or more of these issues may be addressed.

FIG. 6C shows the injection device 500 of FIG. 6B after the user has actuated the latch 550 to hold the needle shroud 518 in its retracted position during medicament delivery. The user has actuated the latch 550 by applying an actuation force to the flap 560 to move it from its initial configuration to an engaged configuration, to cause the flap 560 to engage the needle shroud 518. For example, the user has applied the actuation force to the outer surface of the flap 560 by pressing a finger or thumb directly against the outer surface to push the flap 560 (and more particularly a free end of the flap 560) radially inwards and into the housing 502, causing the engaging element 568 to engage the cooperating element (e.g., slot 572). As the actuation force is applied to the flap 560, the flap 560 is deflected such that it pivots with respect to the remainder of the housing 502 due to the resilient connection between the flap 560 and the remainder of the housing 502, pivoting towards the needle shroud 518 about an axis perpendicular to the longitudinal axis of the injection device 500.

FIG. 6C shows the engaging element 568 engaging the cooperating element. In this example, the engaging element 568 comprises a proximal-facing edge or surface of the flap 560 and the cooperating element comprises the slot 572. Since the flap 560 is prevented from moving axially due to being integrally formed with the housing 502, engagement between the engaging element 568 and the cooperating element prevents the needle shroud 518 from moving axially (at least distally, and optionally proximally) to hold the needle shroud 518 in its retracted position.

Since the needle shroud 518 is held in its retracted position by the flap 560, the biasing force exerted by the control spring on the needle shroud 518 to bias the needle shroud 518 towards its extended position may no longer be transferred by the needle shroud 518 to the injection site. As such, the user may no longer be required to counteract the biasing force of the control spring with a sufficient holding force to hold the injection device 500 steady against the injection site during medicament delivery. The user may find the injection device 500 easier to handle during medicament delivery, which may reduce the risk of pain or discomfort being experienced by the subject receiving the injection, reduce the risk of medicament leakage from the injection site, and/or reduce the risk of incomplete medicament delivery. The reduction in the required holding force may be advantageous for users with impaired dexterity. The safety of the injection device 500 may be increased compared to one or more prior art devices.

The engaging element 568 and the cooperating element may be dimensioned such that axial movement of needle shroud 518 is minimized when the engaging element 568 and the cooperating element are engaged. For example, where the cooperating element comprises a slot 572, the slot 572 may be configured to have a shape (e.g., cross-section) that closely corresponds to the shape (e.g., cross-section) of the engaging element 568. As an example, a width of the slot 572 substantially parallel to the longitudinal axis of the injection device 500 may closely correspond to a width of the engaging element 568 substantially parallel to the longitudinal axis of the injection device 500 (when the flap 560 is in its engaged configuration). The shape (e.g., cross-section and/or width) of the slot 572 may be slightly greater than the corresponding shape (e.g., cross-section and/or width) of the engaging element 568 to provide tolerance for insertion of the engaging element 568 into the slot 572.

Where the cooperating element comprises a slot 572, the needle shroud 518 may be held in its retracted position (i.e., prevented from moving distally) due to engagement between a proximal-facing edge or surface of the engaging element 568 (e.g., the proximal-facing edge or surface of the flap 560) and a distal-facing surface 574 of the slot 572.

Once medicament delivery is complete, the latch 550 may be moved from its engaged configuration back to its initial configuration such that the needle shroud 518 is no longer held by the latch 550 and is free to move distally towards its extended position. FIG. 6D shows the injection device 500 of FIG. 6C in its post-use state, after medicament delivery has been completed and the latch 550 has moved to its initial configuration.

The latch 550 may be biased by a latch biasing mechanism from its engaged configuration to its initial configuration. For example, in the injection device 500 shown in FIG. 6D, the resilient coupling between the flap 560 and the remainder of the housing 502 acts as a latch biasing mechanism, biasing the flap 560 from its engaged configuration to its initial configuration. Due to the presence of the latch biasing mechanism, the user may move the flap 560 back to its initial state by removing the actuation force applied to the outer surface of the flap 560, with the flap 560 automatically pivoting back to its initial position and causing the engaging element 568 to be disengaged from the cooperating element (e.g., slot 572) as the actuation force is reduced. FIG. 6D shows the flap 560 having returned to its initial configuration. Since the engaging element 568 is no longer engaged with the cooperating element, the needle shroud 518 is no longer held in its retracted position and is free to move distally towards its extended state.

As the user removes the injection device 500 from the injection site, the needle shroud 518 moves distally with respect to the housing 502 until it reaches its extended position, covering the needle. In some examples, the injection device 500 may comprise a needle shroud catch that prevents proximal movement of the needle shroud 518 to expose the needle, after the needle shroud 518 has moved distally to cover the needle. The needle shroud catch may be manually or automatically activated, and may increase the safety of the device.

In some examples, the proximal-facing surface of the engaging element 568 and/or the distal-facing surface 574 of the cooperating element may be bevelled such that distal movement of the needle shroud 518 from its retracted position causes the flap 560 to pivot radially outwards towards its initial configuration. FIG. 6C shows the distal-facing surface 574 of the cooperating element (e.g., slot 572) being bevelled (i.e., sloped inwardly such that the distal-facing surface 574 faces both the distal end 526 of the injection device 200 and away from the longitudinal axis of the injection device 500). The distal-facing surface 574 is bevelled such that, once a user removes the actuation force from the flap 560 and the needle shroud 518 moves distally under the biasing force of the control spring, the bevelled distal-facing surface 574 engages the proximal-facing surface of the flap 560 (e.g., a proximal-facing surface or edge of the engaging element 568). Distal movement of the needle shroud 518 causes the distal-facing surface 574 to apply a force to the proximal-facing surface of the flap 560 which, due to the bevel, urges the flap 560 radially outwards and the engaging element 568 out of engagement with the cooperating element (e.g., slot 572). The provision of the bevel may therefore assist with automatic movement of the flap 560 back to its initial configuration, in addition to reducing the risk of the engaging element 568 becoming stuck in engagement with the needle shield 518 under the biasing force of the control spring. While FIG. 6C shows the distal-facing surface of the cooperating element (i.e., slot 572) being bevelled and the proximal-facing surface of the engaging element 568 being square, it should be understood that in other examples the proximal-facing surface of the engaging element 568 may be bevelled and the distal-facing surface 574 of the cooperating element may be bevelled, or both the proximal-facing surface of the engaging element 568 and the distal-facing surface 574 of the cooperating element may be bevelled.

While the injection device 500 described in relation to FIG. 5 and FIGS. 6A to 6D has been described as having a particular medicament delivery mechanism, it should be understood that other suitable forms of medicament delivery mechanism may be used instead, for example as described previously. Furthermore, while it has been described in relation to FIG. 5 and FIGS. 6A to 6D that the injection device 500 is activated to initiate medicament delivery in response to distal movement of the needle shroud 518, it should be understood that other mechanisms (automatic or manual) for initiating medicament delivery may be used in addition or alternatively, for example as described previously.

In some variations of the second embodiment, the engaging element 568 may comprise a protuberance that extends radially inwards from an inner surface of the flap 560, in a similar manner to the engaging element 268 discussed in relation to the first embodiment. In such variations of the second embodiment, the protuberance may act in a similar manner to the protuberance of the engaging element 268 discussed in relation to the first embodiment.

Figure 7A:
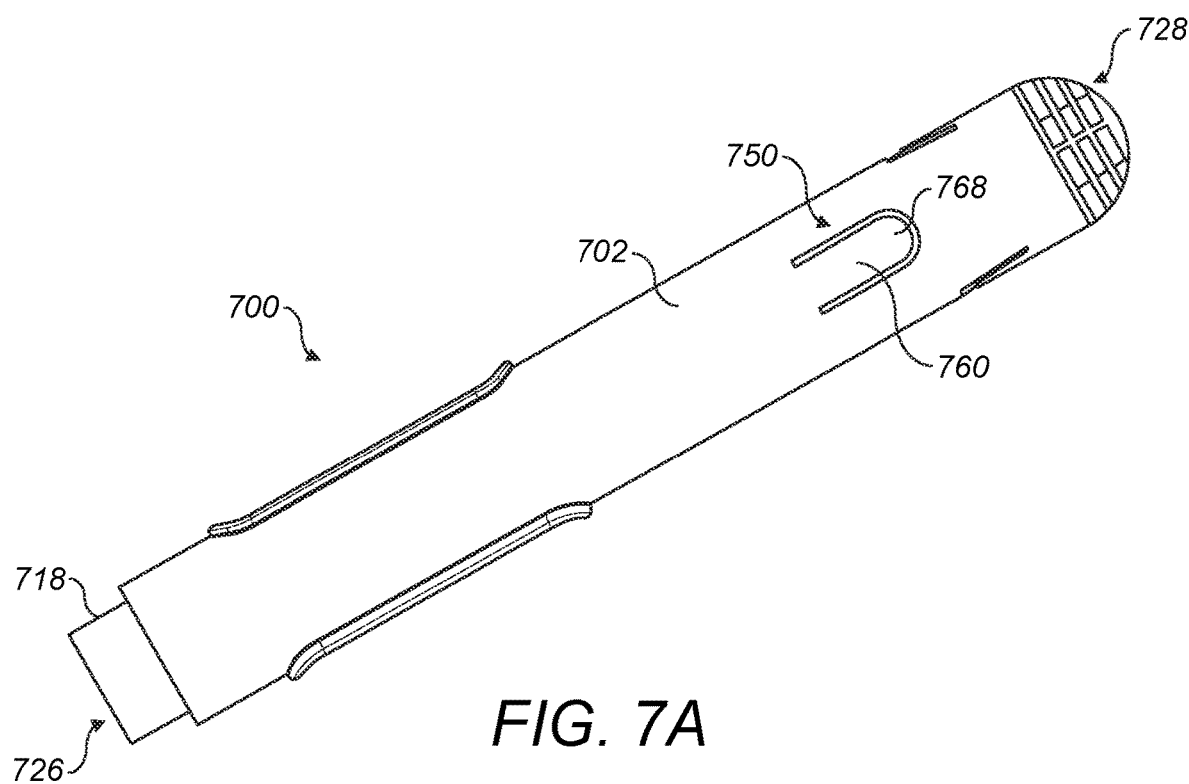
FIG. 7A shows an injection device according to a third embodiment of the present disclosure, in a pre-use state.

FIG. 7A shows an example of an injection device 700 in accordance with a third embodiment of the present disclosure. The injection device 700 may correspond to the injection device 100 of FIG. 1, having one or more features of the injection device 100 of FIG. 1. The injection device 700 is similar to the injection device 200 previously described in relation to FIGS. 2A to 2B and FIGS. 4A to 4D and/or the injection device 500 previously described in relation to FIG. 5 and FIGS. 6A to 6D, however the latch 750 of the injection device 700 takes a different form to the latch 250 of the injection device 200 and the latch 550 of the injection device 500.

The injection device 700 has a distal end 726 and a proximal end 728, and comprises a housing 702 (which may correspond to the casing 102 of FIG. 1). The housing 702 may be cylindrical and extend along the longitudinal axis of the injection device 700. FIG. 7A shows the injection device 700 in a pre-use state, in which a needle shroud 718, in an extended position relative to the housing 702, extends from a distal end of the housing 702 to cover a needle (e.g., needle 116 of FIG. 1). The needle shroud 718 can be moved from its extended position to its retracted position by a user placing a distal end of the needle shroud 718 against an injection site of a subject and applying a force to the housing 702 in a distal axial direction, causing the needle shroud 718 to move axially in a proximal direction with respect to the housing 702 and thereby retract into the housing 702 to expose the needle.

The injection device 700 may comprise a resilient member such as a control spring (e.g., control spring 120) for biasing the needle shroud 718 in a distal direction, from its retracted position towards its extended position. In such circumstances, the user must apply sufficient force to the housing 702 of the injection device 700 to counteract the biasing force exerted on the needle shroud 718 by the control spring so that the needle shroud 718 may be retracted. The user maintains a holding force while pressing the injection device 700 against the injection site until medicament delivery is complete. Counteracting the biasing force may be difficult for some users, for example users with dexterity issues, particularly where the user maintains a holding force for a long period of time during medicament delivery.

The injection device 700 comprises a needle shroud latch 750 for holding the needle shroud 718 in its retracted position relative to the housing 702. The latch 750 is actuated by a user while the needle shroud 718 is in its retracted state to prevent the needle shroud 718 from moving distally with respect to the housing 702 towards its extended position. By holding the needle shroud 718 in its retracted position, the biasing force applied to the needle shroud 718 by the control spring is no longer exerted on the injection site. As such, the user is no longer required to counteract the biasing force while holding the injection device 700 against the injection site.

As shown in FIG. 7A, the latch 750 comprises a button. In the third embodiment, the button and the housing 702 may be integrally formed. The button may comprise a cutout of the housing 702 in the form of a flap 760, the flap 760 integrally formed with the remainder of the housing 702 at one end of the flap 760 (e.g., a distal end, as shown in FIG. 7A). The flap 760 is arranged such that it can be actuated by a user to hold the needle shroud 718 in its retracted position. In this example, the flap 760 is arranged at the side of the injection device 700, at the proximal end 728 of the injection device 700, so that it may be easily actuated by a finger or thumb of the user. However, a different location of the flap 760 may be envisaged.

An outer surface of the flap 760 may be pressed by the user to actuate the flap 760 for holding the needle shroud 718 in its retracted position.

At least a portion of the flap 760 may be resilient such that the flap 760 can be deflected radially inwards in response to the user pressing the outer surface of the flap 760 radially inwards, as described later in relation to FIGS. 8A-D. At least a portion of the flap 760 may be formed from a resilient material to allow for the deflection of the flap 760. An end portion of the flap 760 (which may be a proximal end portion and which may be opposite the end of the flap 760 connected to the remainder of the housing 502) may act as an engaging element 768 for engaging with the needle shroud 718 to hold the needle shroud 718 in its retracted position.

Figure 7B:
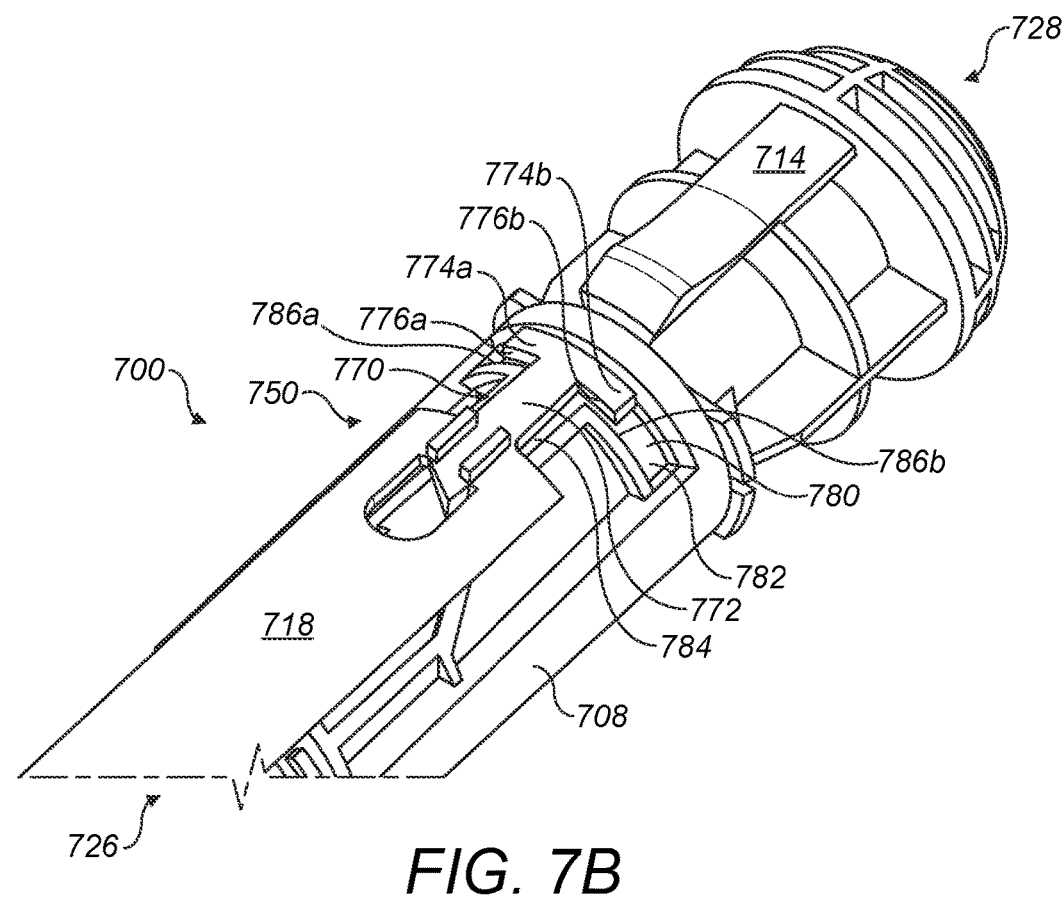
FIG. 7B shows a portion of the injection device of FIG. 7A with a housing of the injection device removed.

FIG. 7B shows a portion of the distal end 728 of the injection device 700 of FIG. 7A with the housing 702 hidden to show various components within the housing 702. As shown in FIG. 7B, the latch 750 further comprises a latch clip 770 and a cooperating element 780. The latch clip 770 is coupled to the needle shroud 718 while the cooperating element 780 is arranged at an outer surface of the collar 708 (which may be similar to the collar 108, 208 and/or 508), however it should be understood that the cooperating element 780 could alternatively be arranged at a different part of the injection device 700, such as a portion of the housing 702 or rear casing 514. The flap 760, latch clip 770 and cooperating element 780 are arranged such that user actuation of the flap 760 causes the flap 760 to engage the latch clip 770, which in turn engages the cooperating element 780 to hold the needle shroud in a retracted position, as described later in more detail in relation to FIGS. 8A to 8D.

As shown in FIG. 7B, the latch clip 770 is 'T'-shaped and extends from the proximal end of the needle shroud 718 in a proximal direction, substantially parallel to the longitudinal axis of the injection device 700 and parallel to the housing 702, the needle shroud 718 and the outer surface of the collar 708. The latch clip 770 may have a substantially similar width in the radial direction (i.e., perpendicular to the longitudinal axis) as the needle shroud 718. The latch clip 770 may be integrally formed with the needle shroud 718.

The latch clip 770 comprises an arm 772 coupled at its distal end to the proximal end of the needle shroud 718 and extending in a proximal direction. At least one latch projection 774a, 774b is formed at the free (e.g., proximal) end of the arm 772, extending out from the arm 772 in a direction substantially perpendicular to the longitudinal axis of the injection device 700. FIG. 7B shows two latch projections 774a and 774b extending from opposite sides of the arm 772, in opposite directions, and substantially perpendicular to the arm 772. The latch projections 774a, 774b may be slightly curved such that the upper (outer) surfaces of the latch projections 774a, 774b closely follow the circumferential inner surface of the housing 702 while the lower surfaces of the latch projections 774a, 774b closely follow the circumferential outer surface of the collar 708. While two latch projections 774a and 774b are shown in FIG. 7B, it should be understood that in alternative embodiments one of the latch projections 774a and 774b may be present, or more than two latch projections 774a, 774b may be present.

FIG. 7B shows the injection device 700 of FIG. 7A when in an activated state, with the needle shroud 718 in its retracted position with respect to the housing 702 (as described later in relation to FIG. 8B). As shown in FIG. 7B, when the needle shroud 718 is in its retracted position, the latch clip 770 is aligned with the cooperating element 780 such that it may be urged into engagement with the cooperating element 780 as later described in relation to FIG. 8C (however, the latch clip 770 is not yet in engagement with the cooperating element 780 in FIG. 7B).

The cooperating element 780 may comprise a slot (e.g., an aperture or recess) formed at the outer surface of the collar 708, the slot having a substantially similar shape to the latch clip 770 (e.g., 'T'-shaped). The slot may comprise a transverse portion 782 arranged to extend circumferentially around a portion of the collar 708, perpendicular to the longitudinal axis of the injection device 700, and an axial portion 784 extending distally from the transverse portion 782, parallel to the longitudinal axis. The transverse portion 782 is arranged to be engaged by the latch projection(s) 774a, 774b and the axial portion 784 is arranged to receive a portion (e.g., proximal portion) of the arm 772 when the latch clip 770 is deflected radially inwards by user actuation of the flap 560, as described later in relation to FIGS. 8A to 8D. A distal-facing surface 776a, 776b of each latch projection 774a, 774b is arranged to engage a respective proximal-facing surface 786a, 786b of the transverse portion 782 when the latch clip 770 is deflected radially inwards to engage with the cooperating element 780.

FIGS. 8A to 8D show a close-up cross-section of a portion of the device 700 in a plane parallel to the longitudinal axis of the device 700, before and after activation of the device 700. More specifically, FIGS. 8A to 8D show portions of the housing 702, needle shroud 718, latch clip 770 and collar 708 of the injection device 700 of FIGS. 7A and 7B. FIGS. 8A to 8D also show one half of the device 700 about the longitudinal axis of the device 700. Features of the device 700 have been omitted from FIGS. 8A to 8D for the sake of clarity, however it should be understood that the device 700 may include any of the features and/or operate in a similar manner as described in relation to the first embodiment and/or the second embodiment, such as in relation to FIGS. 2A-B, FIGS. 3A-D, FIG. 4, FIG. 5, and/or FIGS. 6A-D (such as a similar method of activation, similar medicament dispensing mechanism, etc.).

Figure 8A:
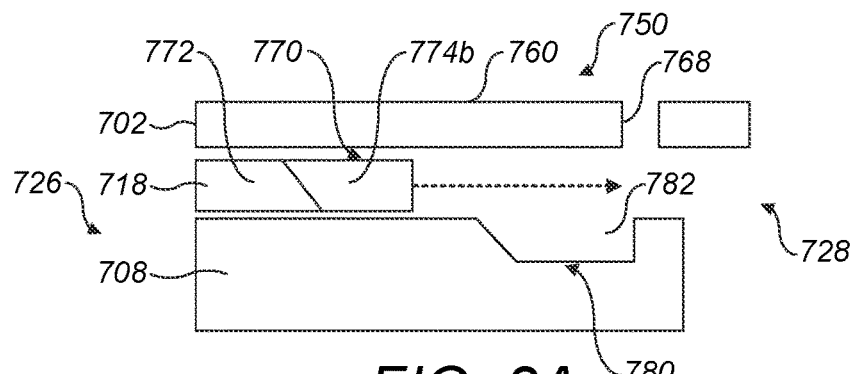
FIG. 8A shows a cross-sectional view of a portion of the injection device of FIG. 7A, in the pre-use state, with a needle shroud in an extended position and the button and a latch clip in respective initial configurations.

FIG. 8A shows the device 700 in its initial, pre-use state. The needle shroud 718 and latch clip 770 are arranged between the inner surface of the housing 702 and the outer surface of the collar 708. The needle shroud 708 of the injection device 700 is not currently being held by a user against an injection site. As such, the needle shroud 718 is in its initial, extended position with respect to the housing 702, in which a distal portion of the needle shroud 718 extends from a distal end of the housing 702 and surrounds a needle to protect the user and the subject (if the subject is different from the user) from the needle. The needle shroud 718 is biased into its extended position by a control spring, which applies a biasing force to the needle shroud 718 to hold the needle shroud 718 in its extended position, in a direction towards the distal end 726 of the injection device 700.

As shown in FIG. 8A, the flap 760 extends substantially parallel to the longitudinal axis of the injection device 700 at the housing 702 and is substantially flush with the outer surface of the remainder of the housing 702. The flap 760 is arranged such that the user is able to press the outer surface of the flap 760 to cause the flap 760 to pivot radially inwards, in some examples through an aperture in the housing 702.

FIG. 8A shows the flap 560 in an initial configuration, in which the flap 560 has not yet been actuated by the user. The engaging element 768 of the flap 760 is aligned with the cooperating element 780 of the collar 708, however the latch clip 770 is coupled to the needle shroud 718 such that, when the needle shroud 718 is in its extended position shown in FIG. 8A, the latch clip 770 is misaligned with the cooperating element 780 and therefore cannot engage the cooperating element 780 to hold the needle shroud 718.

To activate the injection device 700 shown in FIG. 8A for medicament delivery, the user grips the outer surface of the housing 702 and presses the distal end of the needle shroud 718 against the injection site of a subject (which may or may not be the user), applying a distal force to the injection device 700 such that the needle shroud 718 moves axially into the housing 702 in a proximal direction, into its retracted position. The distal force counteracts the biasing force exerted on the needle shroud 718 by the control spring.

Figure 8B:
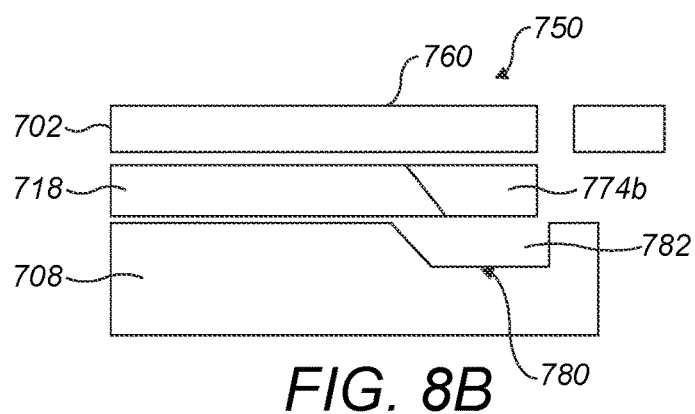
FIG. 8B shows a cross-sectional of the injection device of FIG. 8A in an activated state, with the needle shroud in a retracted position and the button and latch clip in their initial configurations.

FIG. 8B shows the injection device 700 of FIG. 8A now in its activated state, with the needle shroud 718 having moved proximally within the housing 702 into its retracted position. Proximal movement of the needle shroud 718 relative to the needle has uncovered the distal end of the needle, allowing the distal end of the needle to penetrate and extend into the injection site. Proximal movement of the needle shroud 718 has also brought the latch clip 770 into alignment with the engaging element 768 of the flap 760 and the cooperating element 780 of the collar 708 such that the latch clip 770, engaging element 768 and cooperating element 780 are aligned when the needle shroud 718 is in its retracted position. However, FIG. 8B shows that the flap 760 and the latch clip 770 remain in respective initial configurations. When the latch clip 770 is in its initial configuration, it remains substantially parallel to the longitudinal axis of the injection device 700 and has not been deflected by the flap 760 into engagement with the cooperating element 780 of the collar 708. The engaging element 768 does not yet engage the latch clip 770 of the needle shroud 718 (or at least not by an amount that deflects the latch clip 770 into engagement with the cooperating portion 780). If the user were to remove the needle shroud 718 from the injection site at this stage, the needle shroud 718 would be free to move in a distal direction under the biasing force of the control spring, from its retracted position back to its extended position. The user therefore applies a holding force to the housing 702 of the injection device 700 to counteract the biasing force and maintain the needle shroud 718 in its retracted position.

Medicament delivery by a medicament delivery mechanism of the injection device 700 may be activated automatically, for example in response to the retraction of the needle shroud 718 (e.g., in response to retraction of the needle shroud 718 into its retracted position). A plunger within the housing 702 of the injection device 700 may be biased towards the distal end 726 of the injection device 700 by a biasing means, in this example comprising a drive spring. The plunger may be retained in an initial position by a combination of a rear casing 714 and the collar 708 (which may correspond to the rear casing 114 and collar 108 of FIG. 1), preventing the biasing means from displacing the plunger in the distal direction. Retraction of the needle shroud 718 into the housing 702 causes the collar 708 to rotate due to an engagement between the needle shroud 718 and the collar 708, releasing the plunger. Once the plunger has been released, the biasing means causes the plunger to move in the distal direction (i.e., towards the needle end of the injection device 700) by exerting a force on the plunger. The plunger contacts a stopper (e.g., stopper 124 of FIG. 1) in a reservoir of the injection device 700, displacing the stopper in the distal direction and causing medicament stored in the reservoir to be expelled from the injection device 700 via a needle as the plunger moves distally.

The user should hold the injection device 700 in a fixed position with respect to the injection site during medicament delivery until delivery is complete, maintaining their holding force to counteract the biasing force of the control spring. However, certain users such as those with impaired dexterity may have difficulty in holding the injection device 700 steady. For example, the user may have difficulty in maintaining sufficient holding force to keep the needle shroud 718 in its retracted position, particularly when the holding force is applied for a substantial length of time. If the user does not hold the injection device 700 steady, there may be a risk of pain or discomfort for the subject receiving the injection, medicament leakage from the injection site, and/or incomplete medicament delivery. By using the latch 750 of the injection device 700, one or more of these issues may be addressed.

Figure 8C:
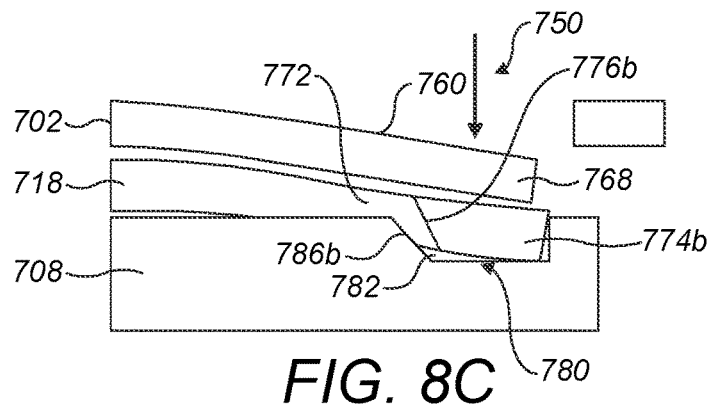
FIG. 8C shows a cross-sectional of the injection device of FIG. 8B in the activated state, with the needle shroud in the retracted position and the button and latch clip in respective engaged configurations.

FIG. 8C shows the injection device 70 of FIG. 8B after the user has actuated the latch 750 to hold the needle shroud 718 in its retracted position during medicament delivery. The user has actuated the latch 750 by applying an actuation force to the flap 760 to move it from its initial configuration to an engaged configuration, to cause the flap 760 to engage the needle shroud 718. For example, the user has applied the actuation force to the outer surface of the flap 760 by pressing a finger or thumb directly against the outer surface to push the flap 760 (and more particularly a free end of the flap 760) radially inwards and into the housing 702, causing the engaging element 768 to engage an upper (outer) surface of the latch clip 770. As the actuation force is applied to the flap 760, the flap 760 is deflected such that it pivots with respect to the remainder of the housing 702 due to the resilient connection between the flap 760 and the remainder of the housing 702, pivoting towards the latch clip 770 and collar 708 about an axis perpendicular to the longitudinal axis of the injection device 700.

FIG. 8C shows the engaging element 768 engaging the upper surface of the latch clip 770, for example an upper (outer) surface of one or more of the latch projections 774a, 774b (wherein first latch projection 774a is obscured behind second latch projection 774b in FIGS. 8A to 8D). In this example, the engaging element 768 comprises a portion of a free end of the flap 760 (such as a portion of the proximal end of the flap 760), however in other examples the engaging element 768 may comprise a protuberance extending from an inner surface of the flap (for example similar to the engaging element 268).

When the needle shroud 718 is in its retracted position, the flap 760, latch clip 770 and cooperating element 780 are arranged such that actuation of the flap 760 from its initial configuration to its engaged configuration causes the latch clip 770 to be deflected radially inwards by the flap 760 to engage the cooperating element 780 of the collar 708. As the user applies an actuation force to the outer surface of the flap 760 to deflect the flap 760 radially inwards, the engaging element 768 of the flap 760 is engages the latch clip 770, which in turn is caused to be deflected radially inwards from its initial configuration to its engaged configuration due to the engaging element 768 transferring at least a portion of the actuation force to the latch clip 770. The latch clip 770 can be deflected to bend radially inwards due to resiliency of the latch clip 770 (e.g. the arm 772) and/or resiliency of at least a portion of the needle shroud 718 (e.g., a proximal end portion of the needle shroud 718). As the latch clip 770 (and more particularly the arm 772) is deflected radially inwards towards the collar 708, the latch clip 770 (and more particularly the one or more latch projections 774a, 774b) is brought into engagement with the cooperating element 780 of the collar 708 such that the needle shroud is held in its retracted position. Put another way, engagement between the latch clip 770 and the cooperating element 780 prevents the needle shroud 718 from moving in a distal direction (e.g. under the biasing force of the control spring), wherein the distal movement of the needle shroud 718 is also brought about by the cooperating element 780 being axially fixed in relation to the housing 702 (e.g., due to the collar 708 being axially fixed with respect to the housing 702) and the deflected flap 760 preventing the latch clip 770 from disengaging from the cooperating element 780.

As shown in FIG. 8C, the latch projection(s) 774a, 774b are received in the transverse portion 782 of the cooperating element 780 such that the distal-facing surface 776a, 776b of each latch projection 774a, 774b are adjacent (e.g. in abutment with, or close to abutment with) a corresponding proximal-facing surface 786a, 786b of the cooperating element 780. Any slight distal movement of the needle shroud 718 will bring the distal-facing surface 776a, 776b of each latch projection 774a, 774b into abutment with its corresponding proximal-facing surface 786a, 786b (if they are not already abutted), with the abutment/engagement between the distal-facing surfaces 776a, 776b and proximal-facing surfaces 786a, 786b preventing further distal movement of the latch clip 770 and needle shroud 718, therefore holding the needle shroud 718 in its retracted position.

Since the needle shroud 718 is held in its retracted position by engagement with the collar 708, the biasing force exerted by the control spring on the needle shroud 718 to bias the needle shroud 718 towards its extended position may no longer be transferred by the needle shroud 718 to the injection site. As such, the user may no longer be required to counteract the biasing force of the control spring with a sufficient holding force to hold the injection device 700 steady against the injection site during medicament delivery. The user may find the injection device 700 easier to handle during medicament delivery, which may reduce the risk of pain or discomfort being experienced by the subject receiving the injection, reduce the risk of medicament leakage from the injection site, and/or reduce the risk of incomplete medicament delivery. The reduction in the required holding force may be advantageous for users with impaired dexterity. The safety of the injection device 700 may be increased compared to one or more prior art devices.

The latch clip 770 and the cooperating element 780 may be dimensioned such that axial movement of needle shroud 718 is minimized when the latch clip 770 and the cooperating element 780 are engaged. For example, where the cooperating element 780 comprises a slot, the slot may be configured to have a shape (e.g., cross-section) that closely corresponds to the shape (e.g., cross-section) of the latch clip 770. As an example, a width of a transverse portion 782 of the cooperating element 780 substantially parallel to the longitudinal axis of the injection device 700 may closely correspond to a width of the latch projection(s) 774a, 774b substantially parallel to the longitudinal axis of the injection device 700 (when the latch clip 770 is in its engaged configuration with the cooperating element 780). The shape (e.g., cross-section and/or width) of the slot may be slightly greater than the corresponding shape (e.g., cross-section and/or width) of the latch clip 770 to provide tolerance for insertion of the latch clip 770 into the slot.

When the latch clip 770 is in its engaged configuration such that it engages the cooperating portion 780, at least a portion of the arm 772 (e.g. a proximal portion of the arm 772) may be received in the axial portion (hidden in FIGS. 8A to 8D) of the cooperating element 780, as indicated by the hidden lower portion of the arm 772 in FIG. 8C.

Figure 8D:
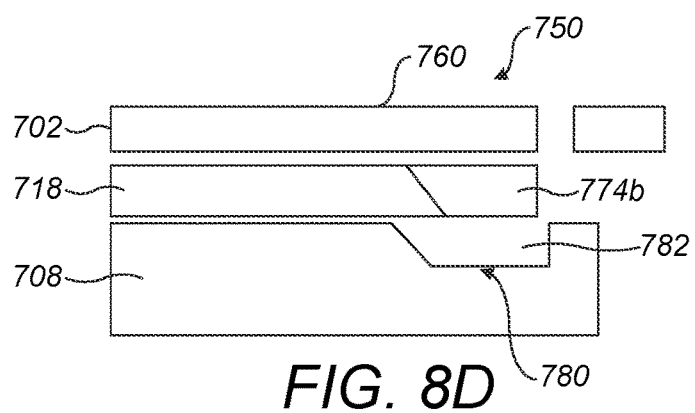
FIG. 8D shows a cross-sectional of the injection device of FIG. 8C in a post-use state, with the needle shroud in the retracted position and the button and latch clip in their initial configurations.

Once medicament delivery is complete, the latch 750 may be moved from its engaged configuration back to its initial configuration such that the needle shroud 718 is no longer held by the latch 750 and is free to move distally towards its extended position. FIG. 8D shows the injection device 700 of FIG. 8C in its post-use state, after medicament delivery has been completed and the latch 750 has moved to its initial configuration.

The latch 750 may be biased by a latch biasing mechanism from its engaged configuration to its initial configuration. For example, in the injection device 700 shown in FIG. 8D, the resiliency of the latch clip 770 (e.g., of the arm 772 of the needle shroud 718) acts as a latch biasing mechanism, biasing the latch clip 770 from its engaged configuration to its initial configuration. Due to the presence of the latch biasing mechanism, the user may move the latch 750 back to its initial state by removing the actuation force applied to the outer surface of the flap 760, with the resiliency of the latch clip 770 causing the latch clip 770 to pivot back to its initial configuration, in turn urging the flap 760 to pivot back towards its initial configuration. In some examples, a resiliency of the flap 760 also acts as part of the latch biasing mechanism, to bias the flap 760 back towards its initial configuration as the actuation force is removed. As the latch clip 770 pivots radially outwards, from its engaged configuration towards its initial configuration, the latch clip 770 (e.g. the latch projection(s) 774a, 774b) disengage from the cooperating element 780 (e.g., the transverse portion 782) as the actuation force is reduced. FIG. 8D shows the latch clip 770 and the flap 760 having returned to their respective initial configurations. Since the latch clip 770 is no longer engaged with the cooperating element 780, the needle shroud 718 is no longer held in its retracted position and is free to move distally towards its extended state.

As the user removes the injection device 700 from the injection site, the needle shroud 718 moves distally with respect to the housing 702 until it reaches its extended position, covering the needle. In some examples, the injection device 700 may comprise a needle shroud catch that prevents proximal movement of the needle shroud 718 to expose the needle, after the needle shroud 718 has moved distally to cover the needle. The needle shroud catch may be manually or automatically activated, and may increase the safety of the device 700.

In some examples, the proximal-facing surface(s) 776a, 776b of the latch projection(s) 774a, 774b and/or the distal-facing surface(s) 786a, 786b of the cooperating element 780 may be beveled such that distal movement of the needle shroud 718 from its retracted position assists with urging the latch clip 770 to be pivoted radially outwards towards its initial configuration (as the actuation force is removed from the flap 760), for example in a similar manner as described in relation to FIG. 4 and FIG. 6A to 6D.

While the injection device 700 described in relation to FIGS. 7A to 7B and FIGS. 8A to 8D has been described as having a particular medicament delivery mechanism, it should be understood that other suitable forms of medicament delivery mechanism may be used instead, for example as described previously. Furthermore, while it has been described in relation to FIGS. 7A to 7B and FIGS. 8A to 8D that the injection device 700 is activated to initiate medicament delivery in response to distal movement of the needle shroud 718, it should be understood that other mechanisms (automatic or manual) for initiating medicament delivery may be used in addition or alternatively, for example as described previously.

While the button described in relation to FIGS. 7A to 7B and FIGS. 8A to 8D has been described as a flap 760, it should be understood that in other examples the button may take a different form, for example similar to the button 260 described in relation FIGS. 2A-B and FIGS. 3A to 3D.

Where the cooperating element 780 comprises a slot, the slot could be a recess or an aperture formed in the collar 708. However, in other examples the cooperating element may take a different form, such as one or more protrusions and/or a friction surface.

In some variations of the third embodiment, the engaging element 768 may comprise a protuberance that extends radially inwards from an inner surface of the flap 760, in a similar manner to the engaging element 268 discussed in relation to the first embodiment. In such variations of the third embodiment, the protuberance may act in a similar manner to the protuberance of the engaging element 268 discussed in relation to the first embodiment.

Figure 9:
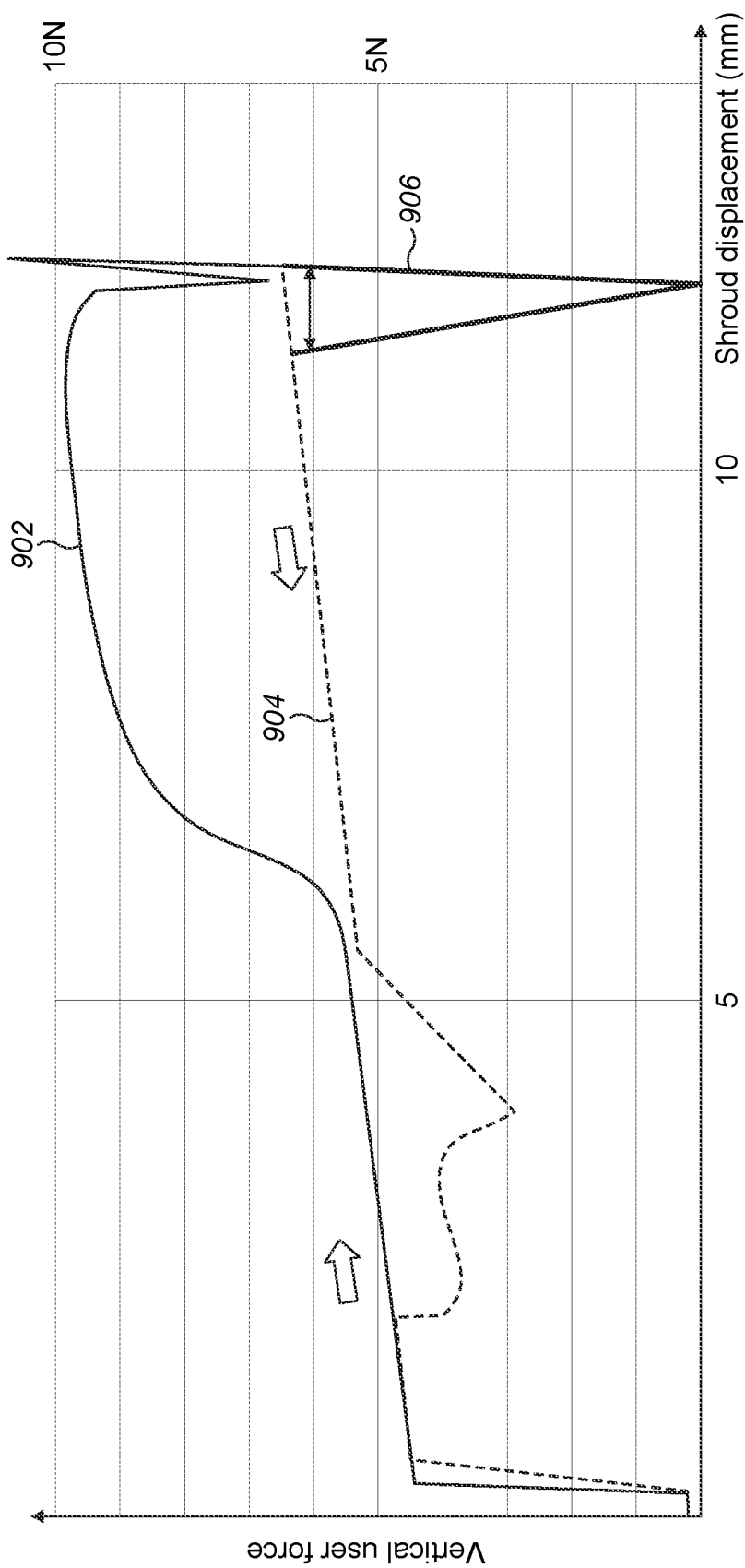
FIG. 9 is a force profile graph illustrating the force profile of one or more injection devices according to the present disclosure.

Referring to FIG. 9, a force profile graph is shown illustrating the force profile of an injection device according to the present disclosure, such as any of the injection devices 200, 500 and/or 700 described herein. The x axis (horizontal axis) is the displacement of the needle shroud of the device in millimeters and the y axis (vertical axis) is the user applied force in Newtons.

The first trace 902 shows the force profile of the activation force of an injection device according to the present disclosure, such as any of the injection devices 200, 500 or 700, when the user is pushing the device onto an injection site. The second trace 904 shows the force profile of the injection device when the user is removing the injection device from the injection site after completion of medicament delivery, wherein the user has not utilized the needle shroud latch (e.g., needle shroud latch 250, 550, or 750) of the injection device during medicament delivery. In other words, the user has not moved the needle shroud latch of the injection device from its initial configuration to its engaged configuration (e.g. by actuating the button 260, 560 or 760 from its initial configuration to its engaged configuration) at any point during the injection procedure. As such, the needle shroud biasing member (e.g., control spring) continues to apply a non-zero biasing force to the needle shroud while the needle shroud is at its maximum displacement within the housing, as indicated by the second trace 904. This biasing force is matched by a corresponding vertical user force if the user is to hold the injection device steady at an injection site.

In order to overcome the biasing force of the needle shroud biasing member, the user may instead utilize the needle shroud latch of the injection device during medicament delivery. In other words, the user may move the button of the latch from its initial configuration to its engaged configuration while the needle shroud is at its maximum displacement, before moving the button back to its initial configuration once medicament delivery is complete. The third trace 906 shows a modification to the force profile of the second trace 904 which occurs when the user has instead utilized the needle shroud latch during medicament delivery. The user has moved the button of the latch from its initial configuration to its engaged configuration while the needle shroud is at its maximum displacement such that the needle shroud biasing member no longer exerts a biasing force on the needle shroud. This is shown in FIG. 9 by the third trace 906 indicating a zero vertical user force near the maximum displacement of the needle shroud. The user therefore is therefore no longer required to provide a corresponding vertical user force to overcome a biasing force of the needle shroud biasing member if the user is to hold the injection device steady at an injection site. Once medicament delivery is complete, the user moves the button back to its initial position to release the needle shroud, after which the force profile of the injection device will once again follow the second trace 904 as the injection device is removed from the injection site.

Figure 10:
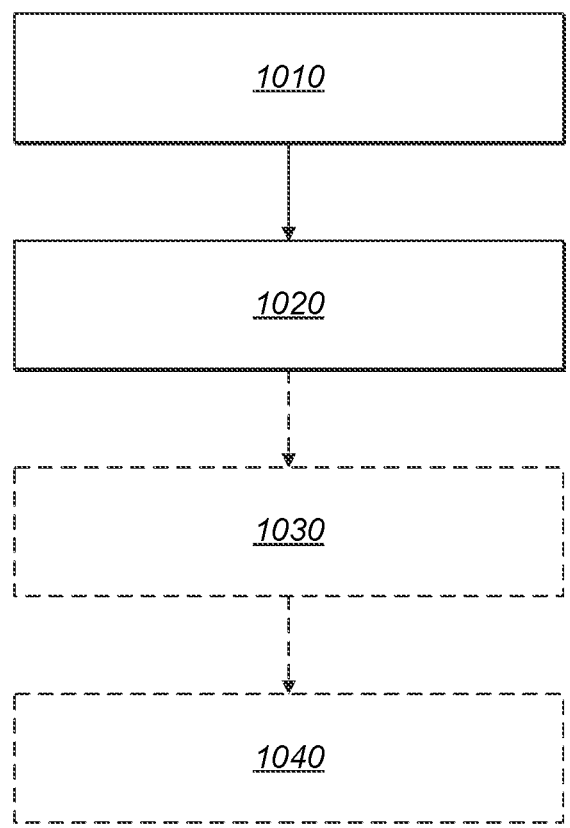
FIG. 10 shows a flow diagram of an example method of holding a needle shroud of an injection device during medicament delivery.

FIG. 10 shows a flow diagram of an example method for holding the needle shroud of an injection device during medicament delivery. The method may correspond to one or more of the operations described in relation to FIGS. 3A to 3D, FIGS. 6A to 6D, and/or FIG. 8A to 8D. The injection device may be the injection device 100, injection device 200, injection device 500, or injection device 700, for example.

At operation 1010, the needle shroud is moved within a housing of the injection device from an extended position to a retracted position, for example in any manner described herein.

At operation 1020, subsequent to moving the needle shroud within a housing of the injection device from the extended position to the retracted position, and while the needle shroud is in the retracted position, the needle shroud latch of the injection device is used (e.g. moved from an initial configuration to an engaged configuration) to hold the needle shroud in its retracted position, for example in any manner described herein.

The needle shroud latch may comprise a button arranged at the housing such that a user can actuate the button, and using the needle shroud latch to hold the needle shroud in its retracted position may comprise actuating the button to hold the needle shroud in its retracted position. The button may take the form of any button described herein.

At optional operation 1030, subsequent to using the needle shroud latch to hold the needle shroud in its retracted position, the needle shroud latch is released (e.g. moved from its engaged configuration to its initial configuration) to release the needle shroud, such that the needle shroud is not held in its retracted position by the needle shroud latch.

At optional operation 1030, subsequent to using the needle shroud latch to hold the needle shroud in its retracted position, the needle shroud latch is released (e.g. moved from its engaged configuration to its initial configuration) to release the needle shroud, such that the needle shroud is not held in its retracted position by the needle shroud latch, for example in any manner described herein.

At optional operation 1040, subsequent to releasing the needle shroud latch, the needle shroud is moved from its retracted position to its extended position (e.g. by removing the injection device from an injection site), for example in any manner described herein.

Any of the injection device described herein such as the injection device 100, 200, 500 and/or 700 could have a length along the longitudinal axis of the injection device of 30 cm or less. For example, the injection device could have a length along the longitudinal axis of the injection device of between 5 cm and 20 cm, between 5 cm and 15 cm, or 10 cm and 20 cm, or between 10 cm and 15 cm. In one or more examples, the injection device may have a length along the longitudinal axis of the injection of approximately 13 cm.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—outer casing/housing
104—reservoir
106—plunger
108—collar
110—cap
112—longitudinal axis
114—rear casing
116—needle
118—needle shroud/sleeve/cover
120—control spring
122—drive spring
124—stopper
126—distal end
128—proximal end
200—injection device
202—housing
204—reservoir
206—plunger 208—collar
214—rear casing
218—needle shroud
219—distal-facing surface (of cooperating element)
222—drive spring
226—distal end
228—proximal end
250—latch
260—button
262—actuation element
264—outer surface
266—arm (of button)
268—engaging element
269—proximal-facing surface (of engaging element)
272—slot
280—aperture (in housing)
500—injection device
502—housing
504—reservoir
506—plunger
508—collar
514—rear casing
518—needle shroud
526—distal end
528—proximal end
550—needle shroud latch
560—flap
568—engaging element (of flap)
572—slot
574—distal-facing surface (or cooperating element)
700—injection device
702—housing
708—collar
718—needle shroud
726—distal end
728—proximal end
750—needle shroud latch
760—flap
768—engaging element (of flap)
770—latch clip
772—arm (of latch clip)
774a, 774b—latch projections
776a, 776b—distal-facing surfaces (of latch projections)
780—cooperating element
782—transverse portion (of cooperating element/slot)
784—axial portion (of cooperating element/slot)
786a, 786b—proximal-facing surfaces (of cooperating element/slot)
902—first trace
904—second trace
906—third trace
1010—(first) operation of method
1020—(second) operation of method
1030—(third) operation of method
1040—(fourth) operation of method

The invention claimed is:

1. An injection device comprising:
a housing;
a needle shroud movable within the housing between an extended position and a retracted position; and
a needle shroud latch configured to hold the needle shroud in the retracted position,
wherein the needle shroud latch comprises a button arranged at the housing such that a user can actuate the button by applying an actuation force to the button, causing the button to contact the needle shroud and hold the needle shroud in the retracted position,
wherein the needle shroud latch further comprises a latch clip coupled to the needle shroud and a cooperating element arranged at a collar of the injection device,
wherein the button, the latch clip, and the cooperating element are arranged such that user actuation of the button causes the button to engage the latch clip, which in turn is caused to engage the cooperating element to hold the needle shroud in the retracted position, and
wherein the latch clip extends from a proximal end of the needle shroud in a proximal direction, substantially parallel to a longitudinal axis of the injection device.

2. The injection device of claim 1,
wherein the button is configured to be actuated by the user from an initial configuration, in which the needle shroud is able to move from the retracted position to the extended position, to an engaged configuration, in which the button holds the needle shroud in the retracted position, and
wherein the button is biased from the engaged configuration to initial configuration.

3. The injection device of The injection device of claim 1,
wherein the button comprises an engaging element, and
wherein the engaging element and the cooperating element are configured such that actuation of the button by the user applying the actuation force to the button causes the engaging element to engage the cooperating portion to hold the needle shroud in the retracted position.

4. The injection device of claim 3, wherein at least one of the engaging element and the cooperating element has a beveled surface.

5. The injection device of claim 1, wherein the button comprises a flap integrally formed with the housing.

6. The injection device of claim 1, wherein the latch clip is biased out of engagement with the cooperating element.

7. The injection device of claim 1, wherein the latch clip is integrally formed with the needle shroud.

8. The injection device of claim 1,
wherein the latch clip comprises an arm extending from the needle shroud and at least one latch projection formed at a free end of the arm,
wherein the latch clip is configured such that engagement of the button with the latch clip due to user actuation of the button causes the arm to be deflected towards the collar such that the at least one latch projection engages the cooperating element to hold the needle shroud in the retracted position.

9. The injection device of claim 1, wherein the cooperating element comprises a slot formed at an outer surface of the collar, wherein the slot is configured to be engaged by the latch clip to hold the needle shroud in the retracted position.

10. The injection device of claim 9, wherein the slot is a recess or an aperture.

11. The injection device of claim 1,
wherein the latch clip comprises an arm extending from the needle shroud and at least one latch projection formed at a free end of the arm,
wherein the cooperating element comprises a slot formed at an outer surface of the collar,
wherein the latch clip is configured such that engagement of the button with the latch clip due to user actuation of the button causes the arm to be deflected towards the collar such that the at least one latch projection engages the slot to hold the needle shroud in the retracted position.

12. The injection device of claim 11, wherein the slot is a recess or an aperture.

13. The injection device of claim 11, wherein a distal-facing surface of the at least one latch projection is arranged to engage a respective proximal-facing surface of the slot when the latch clip is deflected towards the collar.

14. The injection device of claim 13, wherein the distal-facing surface is beveled.

15. The injection device of claim 13, wherein the proximal-facing surface is beveled.

16. The injection device of claim 1,
wherein the injection device comprises a medicament delivery mechanism.

17. The injection device of claim 16, wherein the medicament delivery device comprises a plunger and a drive spring for applying a biasing force to the plunger.

18. The injection device of claim 16, wherein the medicament delivery mechanism is configured to be activated in response to retraction of the needle shroud into the retracted position.

19. The injection device of claim 1, wherein the button is arranged at an outer surface of the housing and at a proximal portion of the housing.

20. The injection device of claim 1, further comprising a control spring configured to apply a biasing force to bias the needle shroud from the retracted position to the extended position.

21. The injection device of claim 20, wherein the control spring does not exert the biasing force on an injection site when the needle shroud is pressed against the injection site and held in the retracted position by the needle shroud latch.

22. The injection device of claim 1, further comprising a reservoir containing a medicament.

23. A method for holding a needle shroud of an injection device during medicament delivery, the method comprising:
moving the needle shroud within a housing of the injection device from an extended position to a retracted position;
subsequent to moving the needle shroud within the housing of the injection device from the extended position to the retracted position, and while the needle shroud is in the retracted position, using a needle shroud latch of the injection device to hold the needle shroud in the retracted position,
wherein the needle shroud latch comprises a button arranged at the housing such that a user can actuate the button, and
wherein using the needle shroud latch to hold the needle shroud in the retracted position comprises actuating the button, causing the button to contact the needle shroud and hold the needle shroud in the retracted position,
wherein the needle shroud latch further comprises a latch clip coupled to the needle shroud and a cooperating element arranged at a collar of the injection device,
wherein the button, the latch clip, and the cooperating element are arranged such that user actuation of the button causes the button to engage the latch clip, which in turn is caused to engage the cooperating element to hold the needle shroud in the retracted position, and
wherein the latch clip extends from a proximal end of the needle shroud in a proximal direction, substantially parallel to a longitudinal axis of the injection device.

24. The method of claim 23, further comprising releasing the needle shroud latch to release the needle shroud.

25. The method of claim 24, further comprising, subsequent to releasing the needle shroud latch, moving the needle shroud from the retracted position to the extended position.

26. The method of claim 23, further comprising dispensing medicament from a syringe of the injection device.

* * * * *